(12) United States Patent
Shanley et al.

(10) Patent No.: US 11,369,754 B2
(45) Date of Patent: Jun. 28, 2022

(54) SYSTEM AND METHOD FOR SAFETY SYRINGE

(71) Applicant: CREDENCE MEDSYSTEMS, INC., Menlo Park, CA (US)

(72) Inventors: Conor Edward Shanley, Emerald Hills, CA (US); Stephen H. Diaz, Palo Alto, CA (US); Alan E. Shluzas, San Carlos, CA (US); Jeff Tillack, Foster City, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 0 days.

(21) Appl. No.: 17/031,108

(22) Filed: Sep. 24, 2020

(65) Prior Publication Data

US 2021/0085891 A1    Mar. 25, 2021

Related U.S. Application Data

(60) Provisional application No. 62/904,988, filed on Sep. 24, 2019.

(51) Int. Cl.
*A61M 5/34* (2006.01)
*A61M 5/32* (2006.01)

(52) U.S. Cl.
CPC .......... *A61M 5/344* (2013.01); *A61M 5/3232* (2013.01); *A61M 5/3293* (2013.01); *A61M 2205/0216* (2013.01)

(58) Field of Classification Search
CPC ........ A61M 5/3221; A61M 2005/3206; A61M 2005/3228
See application file for complete search history.

(56) References Cited

FOREIGN PATENT DOCUMENTS

| WO | WO 91/03269 | 3/1991 | |
|---|---|---|---|
| WO | WO-9103269 A1 * | 3/1991 | .......... A61M 5/3234 |

OTHER PUBLICATIONS

PCT International Search Report and Written Opinion for International Appln. No. PCT/2020/052485, Applicant Magic Leap, Inc., dated Mar. 12, 2021.

* cited by examiner

*Primary Examiner* — Theodore J Stigell
*Assistant Examiner* — Rachel T. Smith
(74) *Attorney, Agent, or Firm* — Vista IP Law Group LLP

(57) ABSTRACT

A syringe assembly includes a syringe body, needle assembly, retaining clip, gasket, needle latch, and needle hub. The syringe body has a syringe interior, longitudinal axis, proximal and distal ends, and needle attachment interface disposed at the distal end thereof. The gasket is configured to be compressed to provide a liquid-tight seal around an outer diameter of the needle assembly and the distal end of the syringe body. The needle latch assembly includes first and second latching tabs configured to retain the needle assembly in a close state and to be plastically deformed to an open state to release the needle assembly, and a gasket backstop configured to provide a flat surface for compression of the gasket, where the first and second latching tabs are spaced apart from the gasket such that neither of the first and second latching tabs contact the gasket during compression of the gasket.

15 Claims, 27 Drawing Sheets

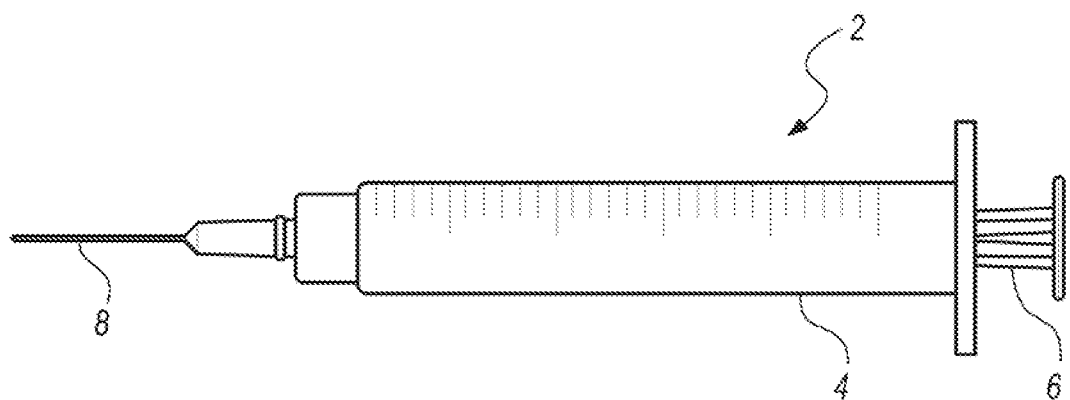
PRIOR ART   FIG. 1A
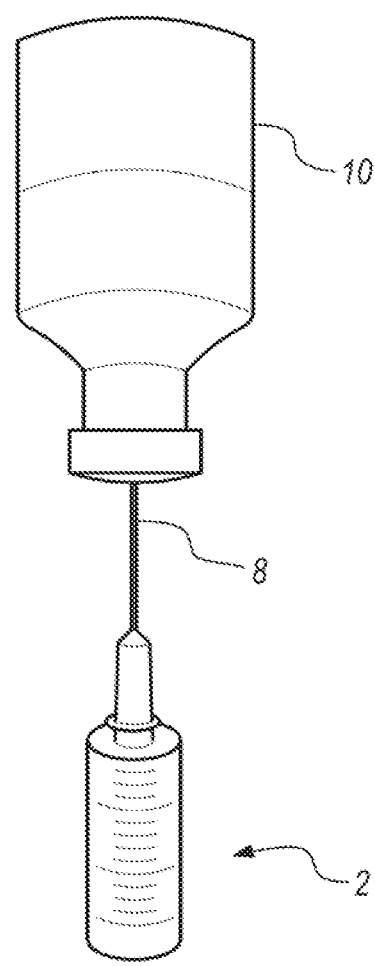
PRIOR ART   FIG. 1B

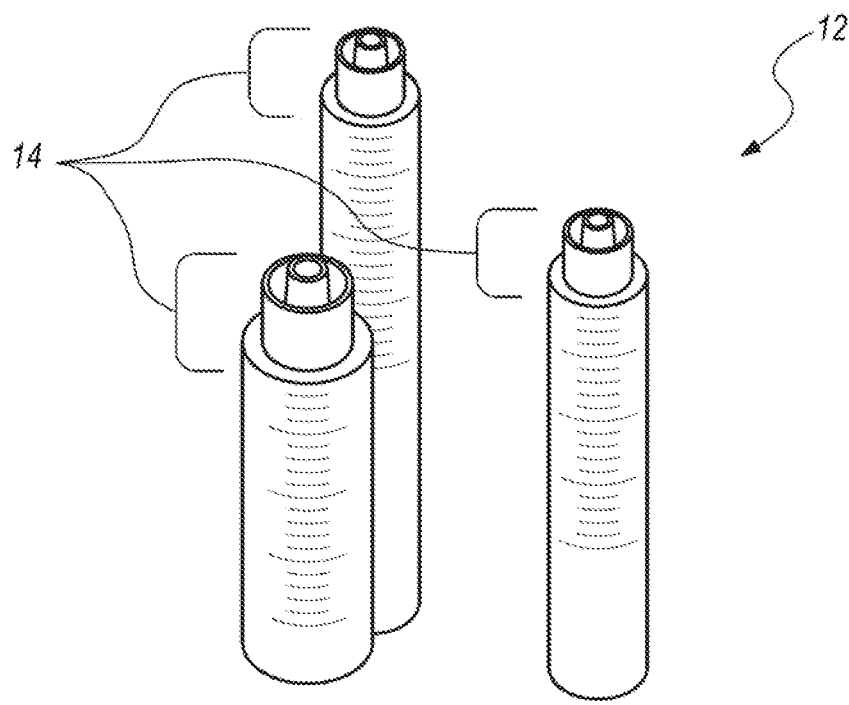
PRIOR ART  FIG. 2A
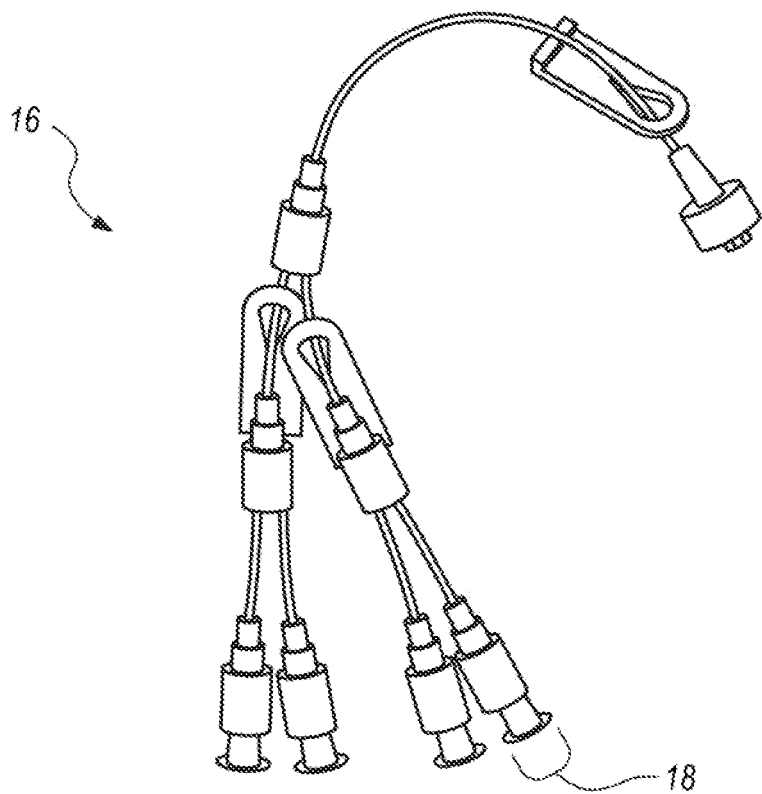
PRIOR ART  FIG. 2B

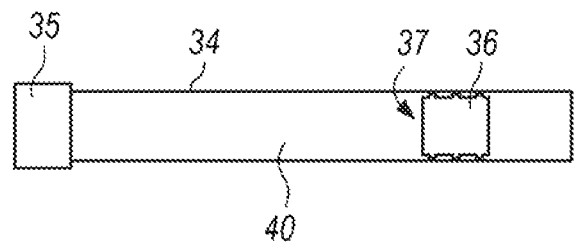
PRIOR ART  *FIG. 5A*
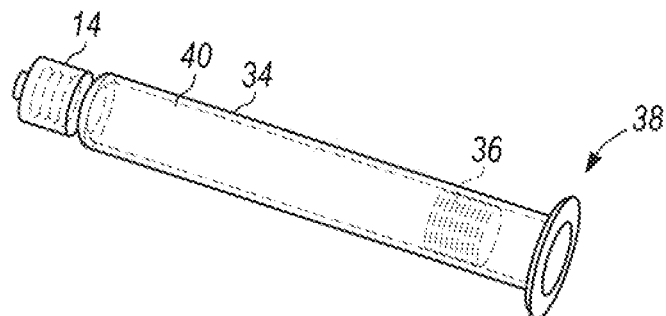
PRIOR ART  *FIG. 5B*
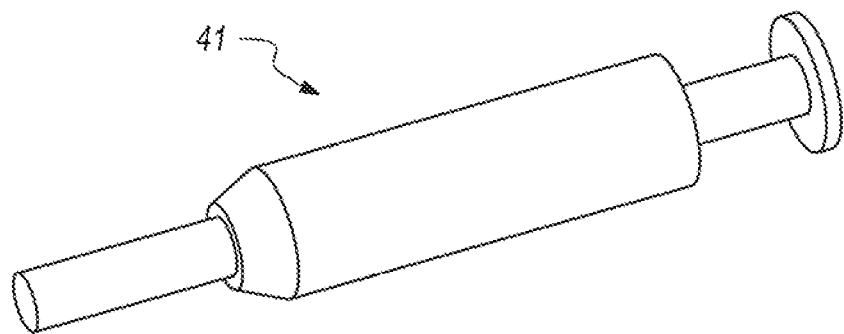
PRIOR ART  *FIG. 5C*

SYSTEM AND METHOD FOR SAFETY SYRINGE

The present application claims priority to (1) U.S. Provisional Patent Application Ser. No. 62/904,988, filed on Sep. 24, 2019, and entitled "SYSTEM AND METHOD FOR SAFETY SYRINGE." This application includes subject matter similar to the subject matter described in the following co-owned U.S. patent applications: (2) U.S. Utility patent application Ser. No. 14/696,342, filed Apr. 24, 2015 and entitled "SYSTEM AND METHOD FOR SAFETY SYRINGE"; (3) U.S. Utility patent application Ser. No. 15/801,281 filed on Nov. 1, 2017 and entitled "CARTRIDGE SAFETY INJECTION SYSTEM AND METHODS"; (4) U.S. Provisional Patent Application Ser. No. 62/827,767 filed on Apr. 1, 2019 and entitled "POLYMERIC INJECTION SYSTEMS"; and (5) U.S. Provisional Patent Application Ser. No. 62/864,509 filed on Jun. 21, 2019 and entitled "SYSTEM AND METHOD FOR SAFETY SYRINGE." The contents of the above-mentioned applications are fully incorporated herein by reference as though set forth in full.

FIELD OF THE INVENTION

The present invention relates generally to injection systems and devices, and more particularly to injection systems and devices related to injection in healthcare environments. Even more particularly, the present invention relates to safe injection systems and devices including retractable needles, and methods for manufacturing, assembling and using same.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling.

The use of needle injection configurations, on the other hand, carries with it the risk of a sharp needle contacting or stabbing a person or structure that is not desired. For this reason, so called "safety syringes" have been developed. One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety. Other "safety syringes" are described in U.S. patent application Ser. Nos. 14/696,342, 14/543,787, 14/321,706, 15/801,239, 15/801,259, 15/801,281, and 15/801,304, the contents of which are fully incorporated herein by reference as though set forth in full.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Some injection system bodies are formed by molding polymers such as Cyclic Olefin Copolymer ("COC") or Cyclic Olefin Polymer ("COP"). Molding injection system bodies is a cost-effective and high throughput method of manufacturing injection system components with an acceptable error rate. For instance, FIG. 6 shows a molded polymer syringe body 600 including an integral luer connector 610 and an inwardly facing thread 612 to facilitate coupling of a needle hub assembly (not shown) onto the molded polymer syringe body 600. The luer connector 610, the inwardly facing thread 612, and the distal end of the syringe body 600 having the inwardly facing thread 612 together form a luer nut 614. The integrated luer nut 614 eliminates the step of attaching a luer nut to the distal end of a syringe body.

Exemplary safe injection systems (e.g., those having polymer injection system bodies) include needle retraction systems such as those described in U.S. patent application Ser. Nos. 14/696,342, 14/543,787, 14/321,706, 15/801,239, 15/801,259, 15/801,281, and 15/801,304, the contents of which have been previously Incorporated by reference herein. Some needle retraction systems include a needle latch assembly that releasably/temporarily couples a needle assembly to a needle hub (and the injection system body/syringe body coupled thereto) until the needle latch assembly is disengaged to allow the needle assembly to be retracted at least partially into the injection system body/syringe body. The needle latch assemblies typically remain latched and are stationary through the injection process during which proximally directed forces of 0.25 lbs. to 0.5 lbs. may be exerted on the needle assembly during penetration of a patient's skin. Retracting the needle assembly moves the sharp needle distal end inside of the needle hub or the injection system body/syringe body to prevent accidental needle sticks. Some existing needle retraction systems include a number of parts that increase system cost and manufacture/assembly complexity.

There is a need for needle retraction systems and components thereof that address the shortcomings of currently-available configurations. In particular, there is a need for a needle latch assembly with a reduced number of parts while retaining the ability to releasably/temporarily couple a needle assembly to a needle hub. Addressing these and other limitations of needle retraction systems allows cost-effective and easy to manufacture data retraction systems to be incorporated into more safe injection systems.

SUMMARY

Embodiments are directed to injection systems. In particular, the embodiments are directed to safe injection systems with needle latch assemblies having a small number (e.g., one or two) of parts to reduce cost and simplify manufacture/assembly.

In one embodiment, a syringe assembly includes a syringe body, a needle assembly, a retaining clip, a gasket, a needle latch, and a needle hub. The syringe body has a syringe interior, a longitudinal axis, proximal and distal ends, and a needle attachment interface disposed at the distal end thereof. The needle assembly having proximal and distal ends. The retaining clip having retention barbs. The gasket is configured to be compressed to provide a liquid-tight seal around an outer diameter of the needle assembly and the distal end of the syringe body. The needle latch assembly includes first and second latching tabs configured to retain the needle assembly in a close state and to be plastically deformed to an open state to release the needle assembly, and a gasket backstop configured to provide a flat surface for compression of the gasket, where the first and second latching tabs are spaced apart from the gasket such that neither of the first and second latching tabs contact the gasket during compression of the gasket. The needle hub having a plurality of interior surfaces configured to retain the needle latch assembly, the gasket, the retaining clip, and the distal end of the syringe body in a sealed configuration to prevent liquid from leaking to the an exterior of the needle hub during injection using the syringe assembly. The needle assembly being configured to be retracted into the syringe body after injection using the syringe assembly.

In one or more embodiments, the needle latch assembly includes a cage including a flat body having a larger opening defined therein, and first and second arms extending orthogonally from the flat body. The first and second latching tabs extend orthogonally from the first and second arms respectively and defining a smaller opening. The larger opening is sized and shaped to allow passage of a needle assembly therethrough. The smaller opening is sized and shaped to prevent passage of the needle assembly therethrough until the first and second latching tabs are deformed.

In one or more embodiments, the first and second latching tabs are plastically deformable. The first and second latching tabs may be configured to plastically deform when 2 lbs. to 3 lbs. of proximally directed force is applied thereto. The first and second latching tabs may be symmetrical. The larger opening may be disposed at a center of the flat body. The smaller opening may be disposed coaxially with the larger opening. The first and second latching tabs may be configured to engage with and disengage from a needle while remaining inside of the cage.

In one or more embodiments, the first and second arms are elastically deformable. The first and second arms may respectively include first and second pairs of standoffs at an opposite end of the cage from the flat body. The first and second pairs of standoffs may be bent toward each other. The first and second arms may be each arcuate when viewed axially. The flat body, the first and second arms, and the first and second latching tabs may be stamped or cut as one piece from a sheet of metal.

In one or more embodiments, the needle latch assembly includes a top flat disc-shaped body having the first and second latching tabs defining a smaller opening, and a larger opening defined therein. The assembly also includes a bottom flat disc-shaped body having an ovoid opening defined therein. The assembly further includes a plurality of joining members coupled to the top and bottom flat disc-shaped bodies such that the ovoid opening defined in the bottom flat disc-shaped body is aligned with the smaller and larger openings defined in the top flat disc-shaped body. The larger opening is sized and shaped to allow passage of a needle assembly therethrough. The smaller opening is sized and shaped to prevent passage of the needle assembly therethrough until the latching tabs are deformed.

In another embodiment, a syringe assembly includes a syringe body, a needle assembly, a retaining clip, a gasket, a needle latch assembly, and a needle hub. The syringe body has a syringe interior, a longitudinal axis, proximal and distal ends, and a needle attachment interface disposed at the distal end thereof. The needle assembly having proximal and distal ends. The retaining clip having retention barbs. The gasket is configured to be compressed to provide a liquid-tight seal around an outer diameter of the needle assembly and the distal end of the syringe body. The needle latch assembly includes a flat disc-shaped body having first and second opposing deformable latching tabs defining a smaller opening, and a larger opening defined therein. The needle hub having a plurality of interior surfaces configured to retain the needle latch assembly, the gasket, the retaining clip, and the distal end of the syringe body in a sealed configuration to prevent liquid from leaking to the an exterior of the needle hub during injection using the syringe assembly. The larger opening is sized and shaped to allow passage of a needle assembly therethrough. The smaller opening is sized and shaped to prevent passage of the needle assembly therethrough until the latching tabs are deformed. The needle assembly being configured to be retracted into the syringe body after injection using the syringe assembly.

In one or more embodiments, the first and second latching tabs are plastically deformable. The first and second latching tabs may be configured to plastically deform when approximately 2 lbs. to 3 lbs. of proximally directed force is applied thereto. The first and second latching tabs may be asymmetrical. The force to plastically deform the latching tabs and release the needle for retraction may be tuned to match the intended needle insertion force requirements. Typically, 0.25 to 0.5 lbf of force is required to pierce the skin and/or insert the needle to the injection depth. The latching tabs are sized to produce approximately 2-3 lbf of needle retention force, resulting in a margin of release force/penetration force of between 4 and 12 (2/0.5=4 to 3/0.25=12). A needle retention force margin above the needle pierce force is desired to ensure needle retraction while overcoming friction between the skin and the needle, the stopper and the needle, and/or friction in the retraction mechanism. In some instances where tissue is denser a higher needle release force of between 3 lbf. and 5 lbf. may be desired. In other instances, where tissue density is lower, a lower needle release force of between 1.0 and 2.0 may be desired. The retraction spring is sized to provide a needle retraction force which is larger than the needle retention force to ensure that the needle is retracted reliably. A larger force retraction spring typically provides a quicker needle retraction, while a smaller force retraction spring typically provides a slower retraction. The larger opening may be disposed eccentrically relative to a center of the flat disc-shaped body. The smaller opening may be disposed at a center of the flat disc-shaped body.

In one or more embodiments, the flat disc-shaped body is stamped or cut from a sheet of metal. The top and bottom flat disc-shaped bodies and the plurality of joining members may be stamped or cut as one piece from a sheet of metal. Metal is the preferred material for the disc as it is easily created by stamping and is creep resistant. Alternatively, the disc may be formed from a polymer or from a rubber material.

In one or more embodiments, the flat disc-shaped body also has an "H" shaped opening defined therein. The flat disc-shaped body may also have a side opening defined therein opposite of the larger opening, where the side opening is continuous with the "H" shaped opening and an exterior of the flat disc-shaped body. The flat disc-shaped body may also have an elastically deformable section disposed adjacent the larger opening and opposite of the side opening. The flat disc-shaped body may be configured to elastically deform at the elastically deformable section in a plane of the flat disc-shaped body to enlarge the side opening. The flat disc-shaped body is configured to elastically deform at the elastically deformable section out of a plane of the flat disc-shaped body to enlarge the side opening.

In still another embodiment, a syringe assembly includes a syringe body, a needle assembly, a retaining clip, a gasket, a needle latch assembly, and a needle hub. The syringe body has a syringe interior, a longitudinal axis, proximal and distal ends, and a needle attachment interface disposed at the distal end thereof. The needle assembly having proximal and distal ends. The retaining clip having retention barbs. The gasket is configured to be compressed to provide a liquid-tight seal around an outer diameter of the needle assembly and the distal end of the syringe body. The needle latch assembly includes a rectangular prism retaining portion sized and shaped to be disposed in space defined in a needle hub. The assembly also includes a cylindrical collar portion sized and shaped to prevent passage of a needle assembly therethrough until the cylindrical collar portion is deformed. The assembly further includes a joining portion coupled to the rectangular prism retaining portion and the cylindrical collar portion. The needle hub having a plurality of interior surfaces configured to retain the needle latch assembly, the gasket, the retaining clip, and the distal end of the syringe body in a sealed configuration to prevent liquid from leaking to the an exterior of the needle hub during injection using the syringe assembly. The needle assembly being configured to be retracted into the syringe body after injection using the syringe assembly.

In one or more embodiments, the rectangular prism retaining portion includes a pair of outwardly biased latching tabs sized and shaped to retain the rectangular prism retaining portion in the space defined in the needle hub. The cylindrical collar portion may include a rolled sheet having a longitudinal opening therein to facilitate deformation of the cylindrical collar portion. The cylindrical collar portion may be plastically deformable. The cylindrical collar portion may be configured to plastically deform when 2 lbs. to 3 lbs. of proximally directed force is applied thereto. The rectangular prism retaining portion, the cylindrical collar portion, and the joining portion may be stamped or cut as one piece from a sheet of metal.

The aforementioned and other embodiments of the invention are described in the Detailed Description which follows.

BRIEF DESCRIPTION OF THE DRAWINGS

The drawings described below are for illustration purposes only. The drawings are not intended to limit the scope of the present disclosure. The foregoing and other aspects of embodiments are described in further detail with reference to the accompanying drawings, in which the same elements in different figures are referred to by common reference numerals, wherein:

FIGS. 1A to 5C illustrate various aspects of conventional injection syringe configurations.

Figure 3:
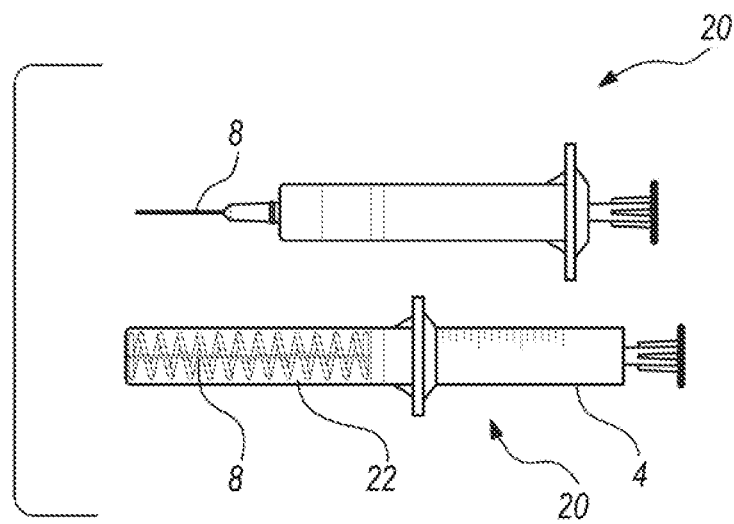
Figure 4A:
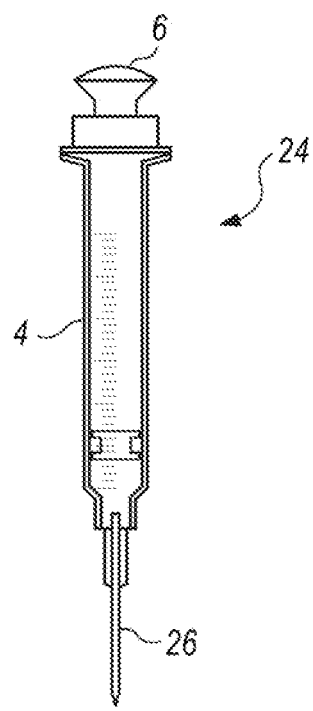
Figure 4B:
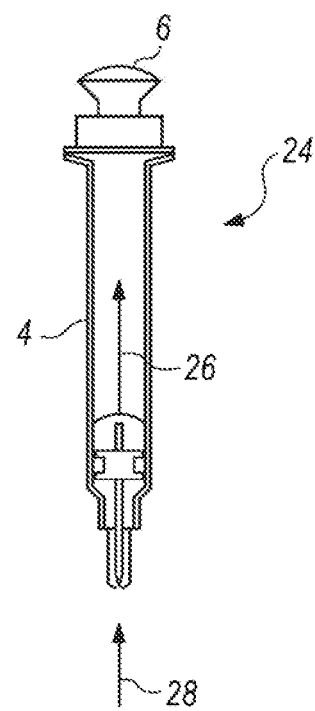
Figure 6:
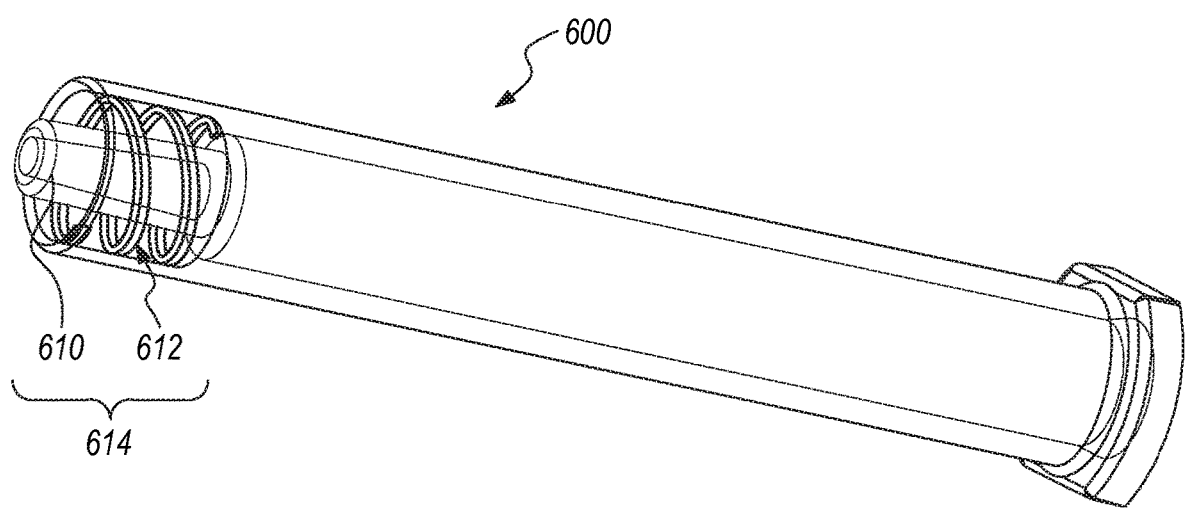
FIG. 6 is a perspective view of a molded polymer injection system body for use with the needle latch assemblies according to some embodiments.

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Safe Injection System

Figure 7A:
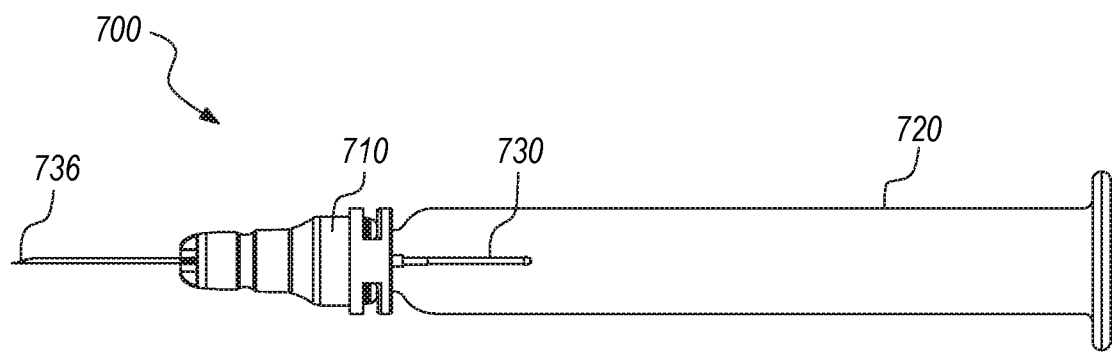
FIGS. 7A and 7B are side and perspective views of a partially assembled safe injection system according to some embodiments.
Figure 7B:
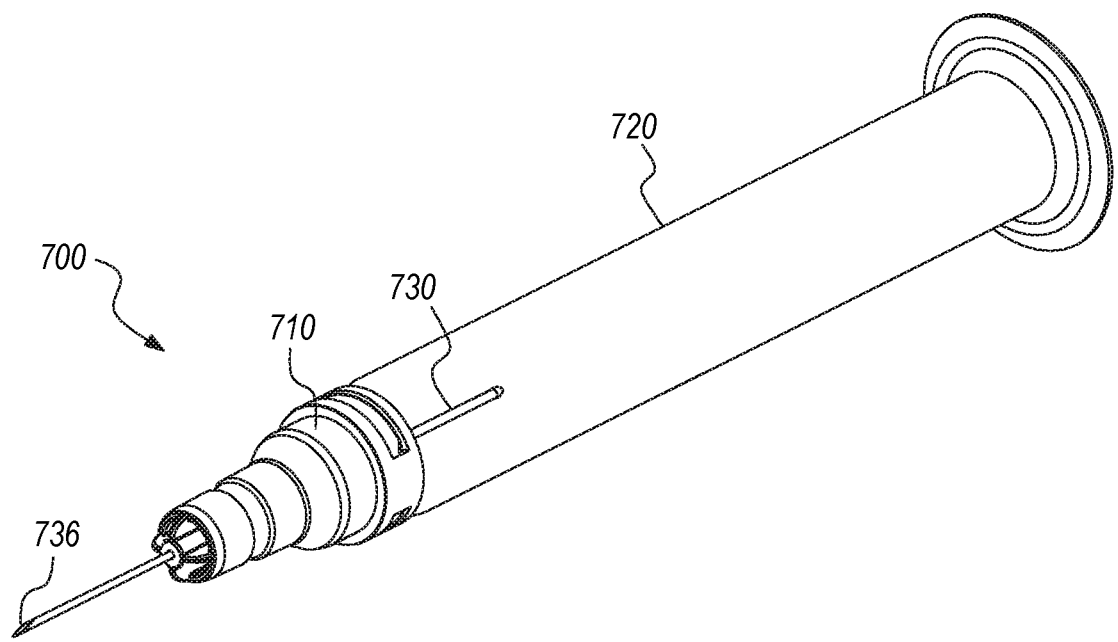

FIGS. 7A and 7B depict a partially assembled safe injection system 700 according to some embodiments. The safe injection system 700 includes a needle hub assembly 710 coupled to a syringe body 720. The syringe body 720 may be a molded polymer syringe body such as those described above and in U.S. patent application Ser. Nos. 62/864,509 and 62/827,767, the contents of which have been previously Incorporated by reference herein. The needle hub assembly 710 includes a needle assembly 730 such as those described below and in U.S. patent application Ser. Nos. 14/696,342, 14/543,787, 14/321,706, 15/801,239, 15/801,259, 15/801,281, and 15/801,304, the contents of which have been previously Incorporated by reference herein.

Although not shown in FIGS. 7A and 7B, the safe injection system 700 includes a needle retraction system such as those described in U.S. patent application Ser. Nos. 14/696,342, 14/543,787, 14/321,706, 15/801,239, 15/801,259, 15/801,281, and 15/801,304, the contents of which have been previously Incorporated by reference herein. The needle retraction system (not shown) exerts a proximally directed force on the needle assembly 730 after injection is completed to pull the needle assembly 730 at least partially inside of the needle hub assembly 710 and/or the syringe body 720 such that the sharp distal tip 736 of the needle assembly 730 is disposed in the needle hub assembly 710 and/or the syringe body 720 to prevent accidental needle sticks. In some embodiments, the proximally directed force is from about 2 lbs. to about 3 lbs.

The needle hub assembly 710 includes a needle latch assembly (various embodiments shown and described below) configured to releasably couple the needle assembly 730 to the needle hub assembly 710 in a latched configuration. In the latched configuration, the needle latch assembly 710 prevents movement of the needle assembly 730 relative to the needle hub assembly 710 and the syringe body 720 coupled thereto. When the needle latch assembly transitions from the latched configuration to an unlatched configuration, the needle assembly 730 is no longer coupled to the needle hub assembly 710, and is therefore free to move relative to the needle hub assembly 710 and the syringe body 720. In other words, in the unlatched configuration, the needle latch assembly allows the needle assembly 730 to be retracted at least partially into the needle hub assembly 710 and/or the syringe body 720 as described above.

Exemplary Flat Disc-Shaped Needle Latch Assemblies

FIGS. 8A to 16D depict various flat disc-shaped needle latch assemblies and their incorporation into needle hub assemblies and safe injection systems according to various embodiments.

Figure 8A:
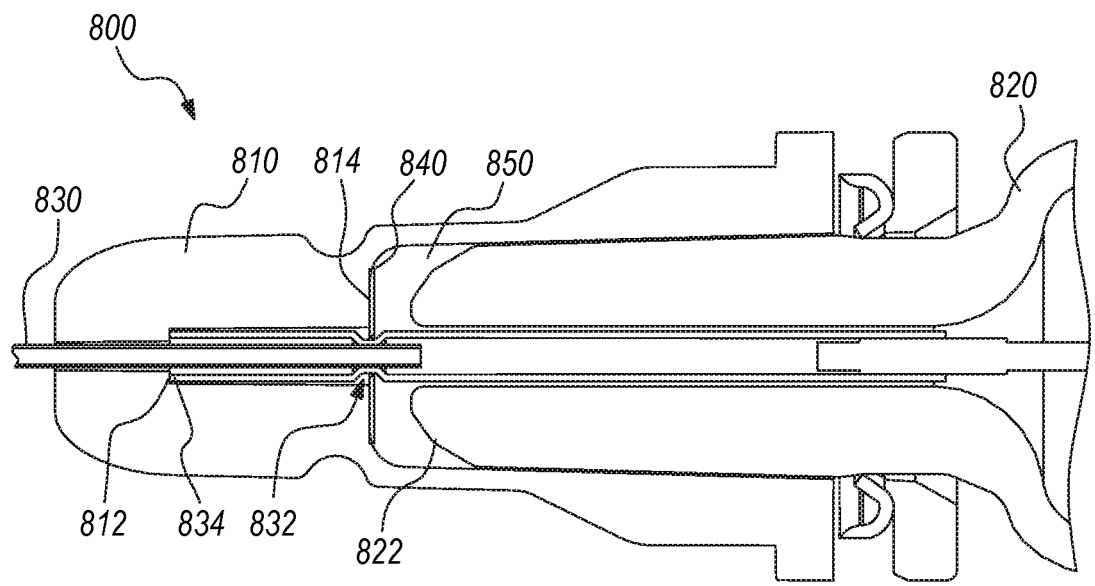
FIGS. 8A and 8B are longitudinal cross-sectional and perspective cut away views of a safe injection system according to some embodiments.
Figure 8B:
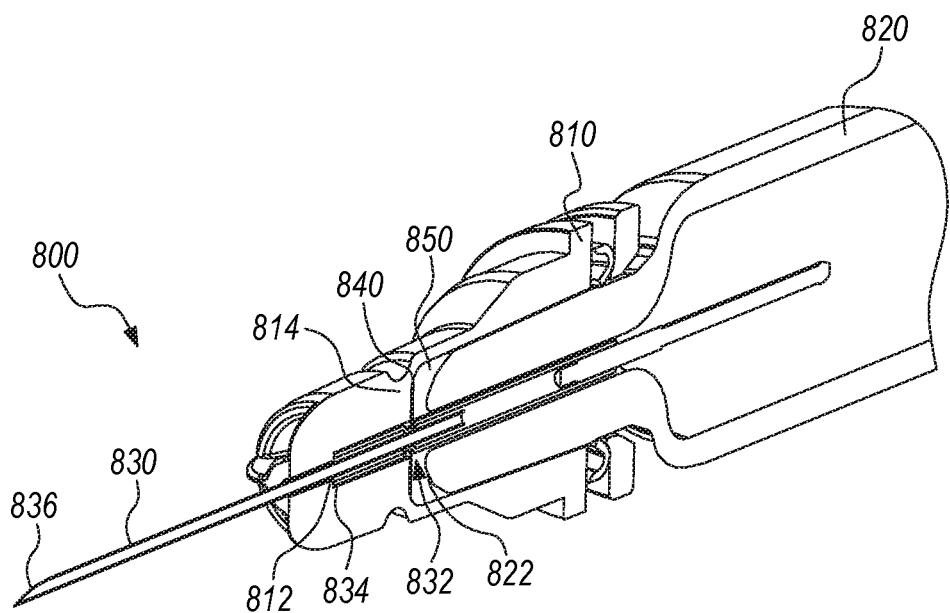
Figure 12A:
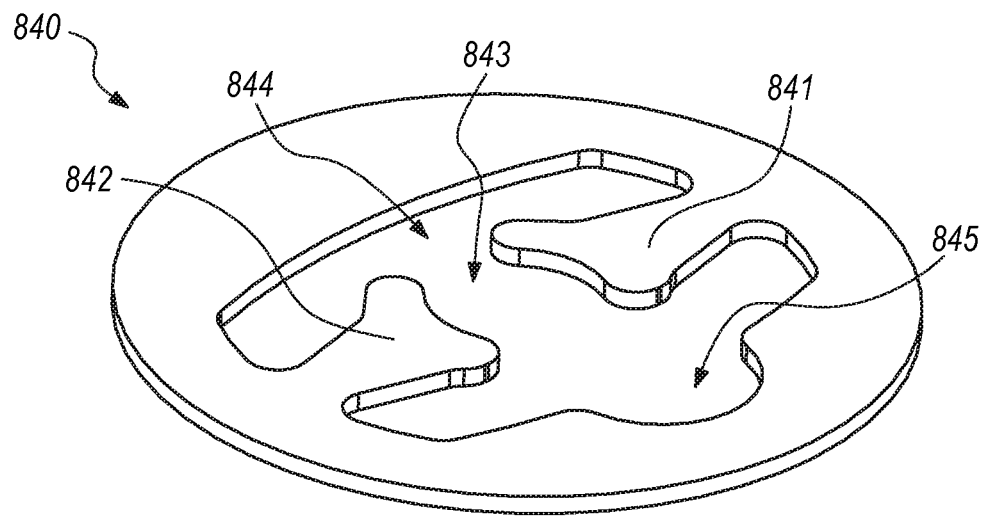
FIGS. 12A and 12B are perspective and top views of a needle latch assembly or components thereof according to some embodiments.
Figure 12B:
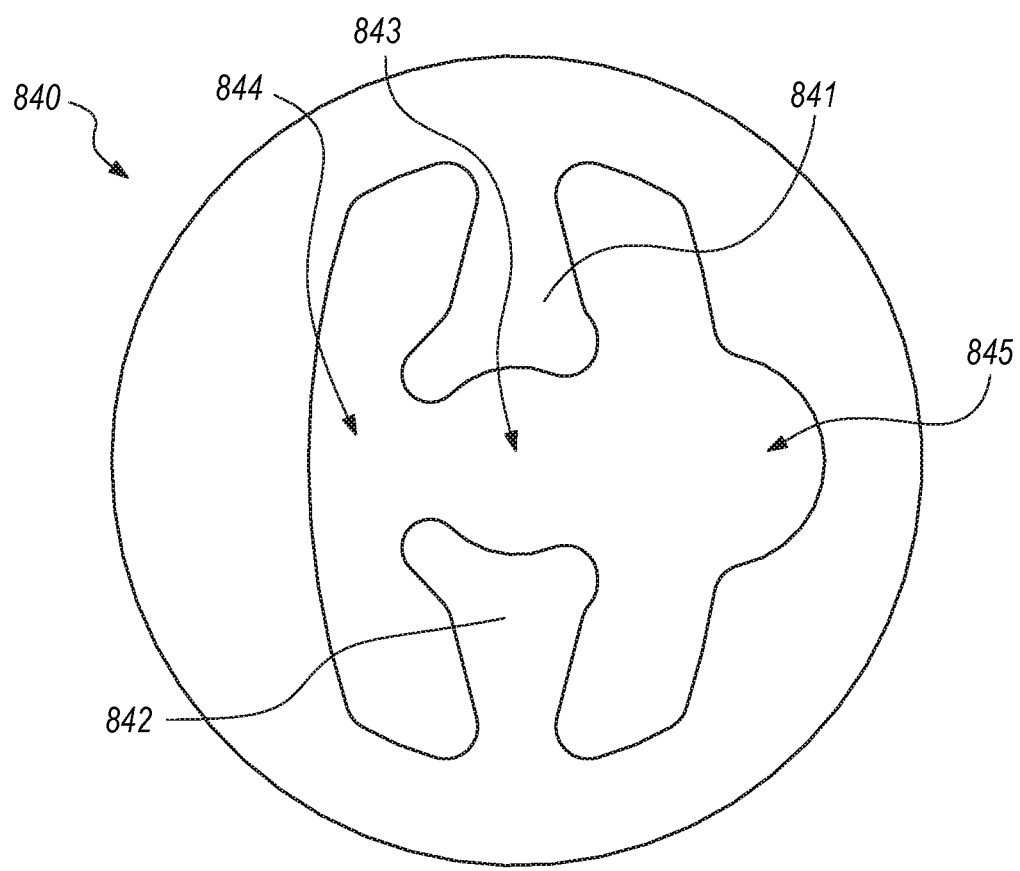
Figure 13A:
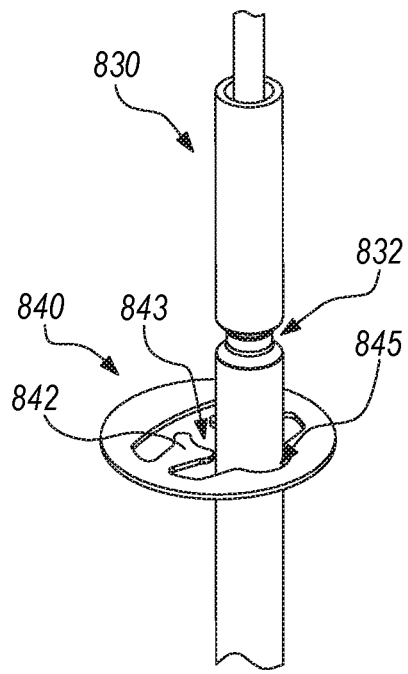
FIGS. 13A to 14B are perspective (FIGS. 13A, 13B, and 14A) and top views (FIGS. 13C and 14B) of a needle latch assembly or components thereof being mounted onto a needle assembly according to some embodiments.
Figure 13B:
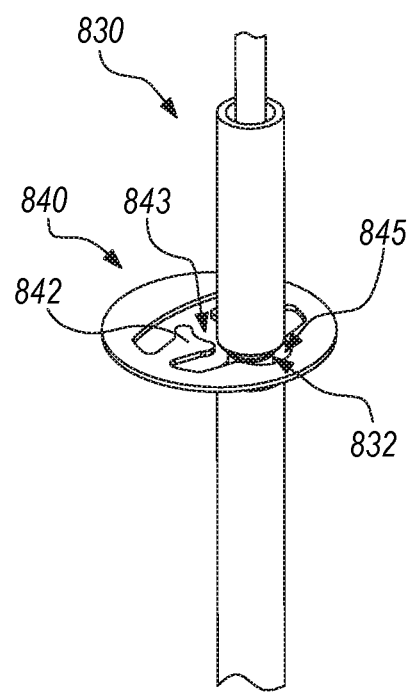
Figure 13C:
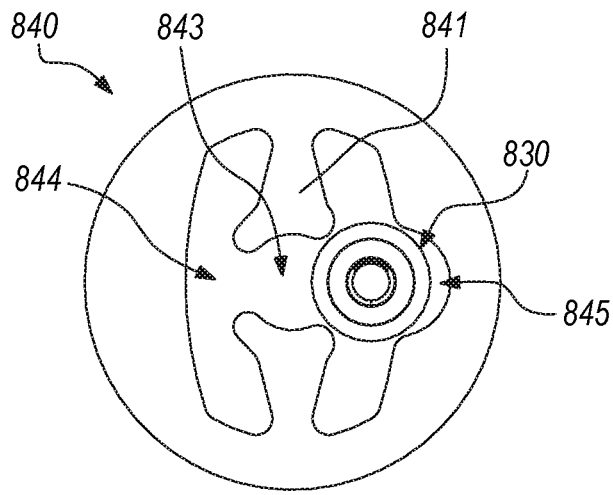
Figure 14A:
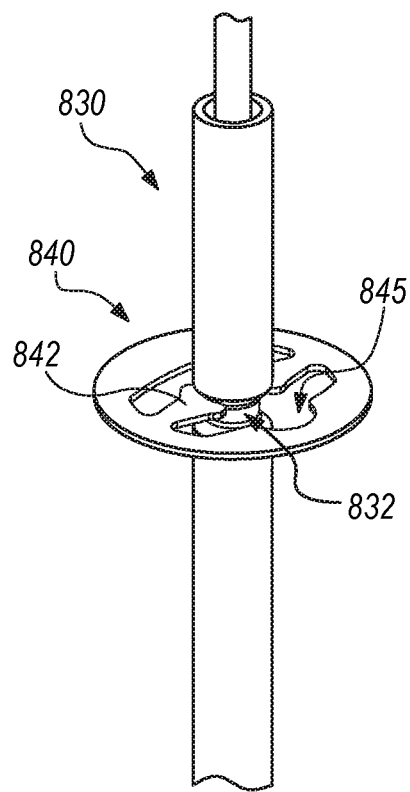
Figure 14B:
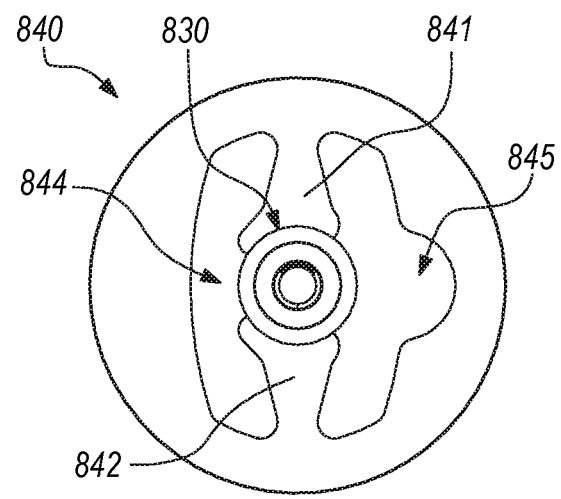

FIGS. 8A and 8B depict a safe injection system 800 according to some embodiments. FIGS. 8A and 8B depict a safe injection system 800 in an assembled and ready to use configuration. The safe injection system 800 includes a needle hub assembly 810 coupled to a syringe body 820 and a needle assembly 830. The syringe body 820 has a syringe interior, a longitudinal axis, proximal and distal ends, and a needle attachment interface disposed at the distal end thereof. The needle hub assembly 810 includes a needle latch assembly 840 configured to releasably interfere with a notch 832 on the needle assembly 830 to releasably couple the needle assembly 830 to the needle hub assembly 810. The needle latch assembly 840 is a flat disc/ring as shown in FIGS. 12A and 12B and described below.

The safe injection system 800 also includes a deformable sealing member/gasket 850 disposed between a distal end 822 of the syringe body 820 a proximal side of the needle latch assembly 840. The deformable sealing member 850 may take the form of an elastomeric polymer disc/ring such that when the safe injection system 800 is assembled, the deformable sealing member 850 fills the space in the needle hub assembly 810 holding the needle latch assembly 840 to provide a fluid tight seal.

Figure 9A:
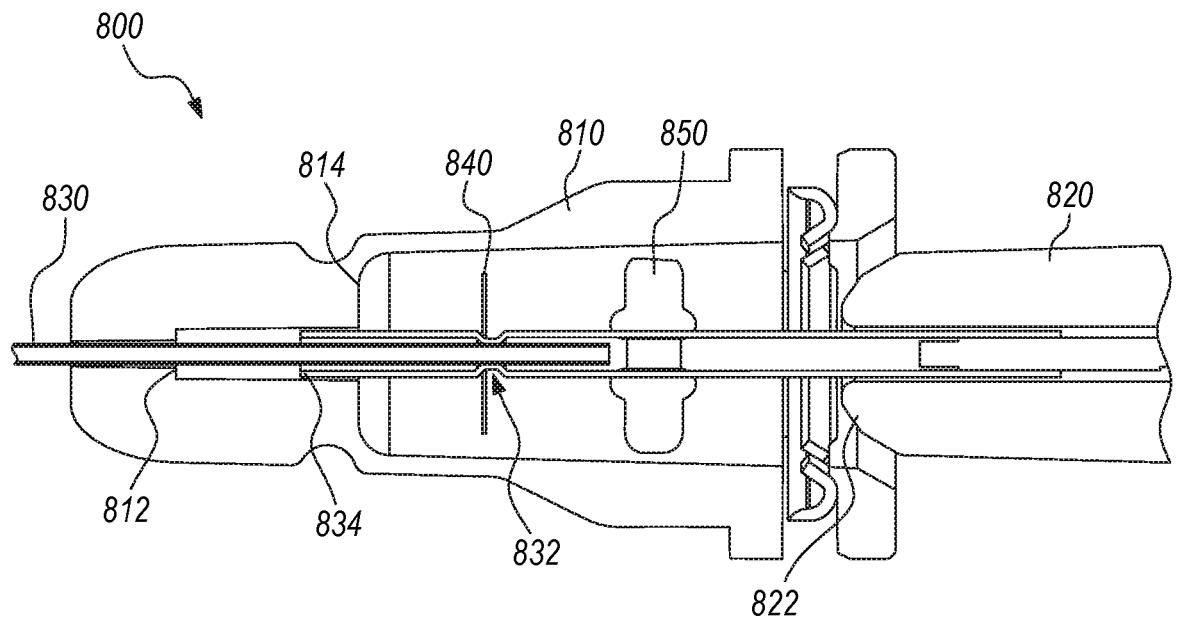
FIGS. 9A and 9B are longitudinal cross-sectional and perspective cut away exploded views of a safe injection system according to some embodiments.
Figure 9B:
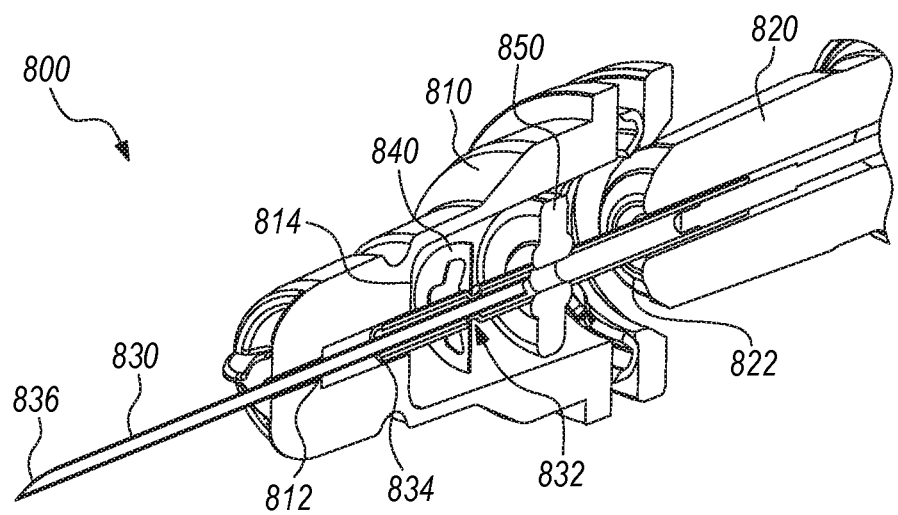

FIGS. 9A and 9B depict the safe injection system 800 in two exploded views to more clearly illustrate the components thereof. As shown in FIGS. 9A and 9B, the needle assembly 830 includes a distal shoulder 834 that interferes with a proximal shoulder 812 formed on an interior surface of the needle hub assembly 810 to limit distal movement of the needle assembly 830 relative to the needle hub assembly 810. FIGS. 8A and 8B illustrate the distal shoulder 834 of the needle assembly 830 abutting the proximal shoulder 812 of the needle hub assembly 810 to limit distal movement of the needle assembly 830 relative to the needle hub assembly 810. FIGS. 9A and 9B also depict the deformable sealing member 850 in an uncompressed/relaxed state. FIGS. 8A and 8B depict the deformable sealing member/gasket 2450 in a compressed/biased state.

Figure 10A:
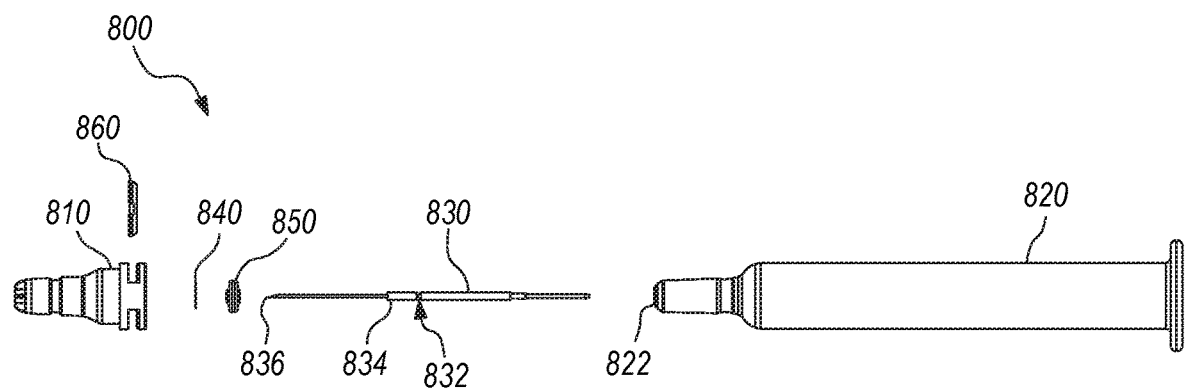
FIGS. 10A and 10B are side and perspective exploded views of components of a safe injection system according to some embodiments.
Figure 10B:
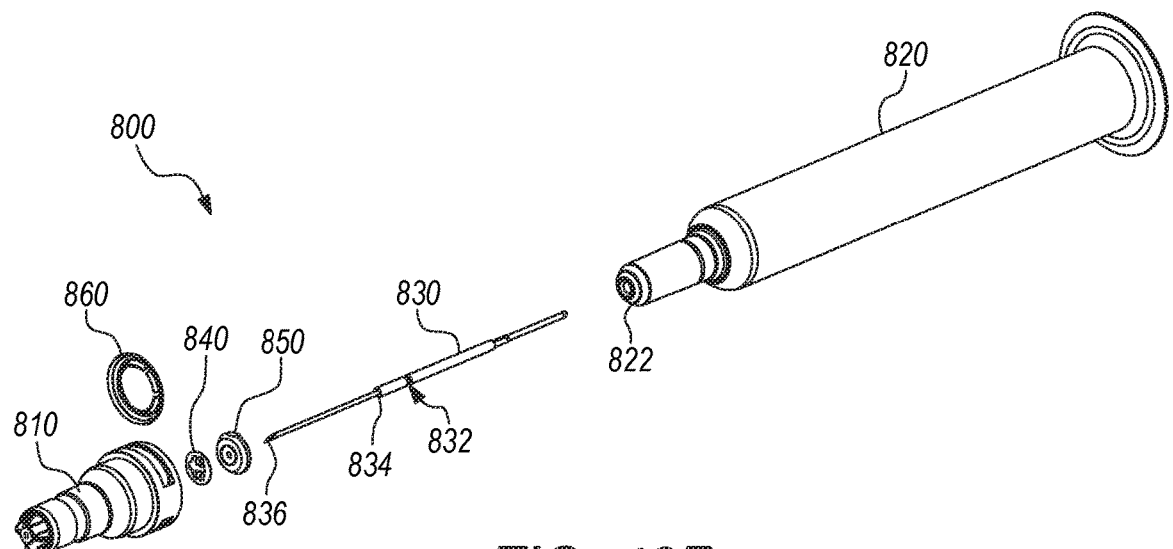

FIGS. 10A and 10B depict the safe injection system 800 in two further exploded views to more clearly illustrate the components thereof. The safe injection system 800 also includes a needle hub retaining ring/retaining clip 860 having retaining barbs configured to allow the needle hub assembly 810 to move proximally relative to the syringe body 820 (e.g., a molded polymer syringe body) while preventing the needle hub assembly 810 from moving distally relative to the syringe body 820 after the two parts have been coupled together during assembly. Further details regarding the needle hub retaining ring 860 are described in U.S. patent application Ser. No. 62/827,767, the contents of which have been previously Incorporated by reference herein.

During manufacturing/assembly of a safe injection system according to some embodiments, the needle latch assembly 840 and the deformable sealing member 850 are threaded over the needle assembly 830 until the needle latch assembly 840 is partially disposed in the notch 832 of the needle assembly 830 and held in place by the deformable sealing member 850 on a proximal side thereof. Then the needle hub assembly 810 with the needle hub retaining ring 860 inserted therein is threaded over the distal end 836 of the needle assembly until the distal shoulder 834 on the needle assembly 830 abuts the proximal shoulder 812 on the needle hub assembly 810. The needle assembly 830 is configured such that when the distal shoulder 834 thereon abuts the proximal shoulder 812 on the needle hub assembly 810, the needle latch assembly 840 abuts a proximal interior wall 814 on the needle hub assembly 810. Next, the syringe body 820 is threaded over the proximal end of the needle assembly 830 and advanced distally until the distal end 822 of the syringe body 820 abuts the proximal side of the deformable sealing member 850. The distal end 822 of the syringe body 820 compresses the deformable sealing member 850 until it fills the space in the needle hub assembly 810 holding the needle latch assembly 840 to provide a fluid tight seal. Then other portions of the safe injection system (e.g., stopper members, the plunger members, etc.) are added to the syringe body 822 complete manufacture/assembly of the safe injection system.

While the method of manufacturing/assembling a safe injection systems described above includes various actions in a particular order, methods according to some other embodiments may include actions in different orders.

Figure 11A:
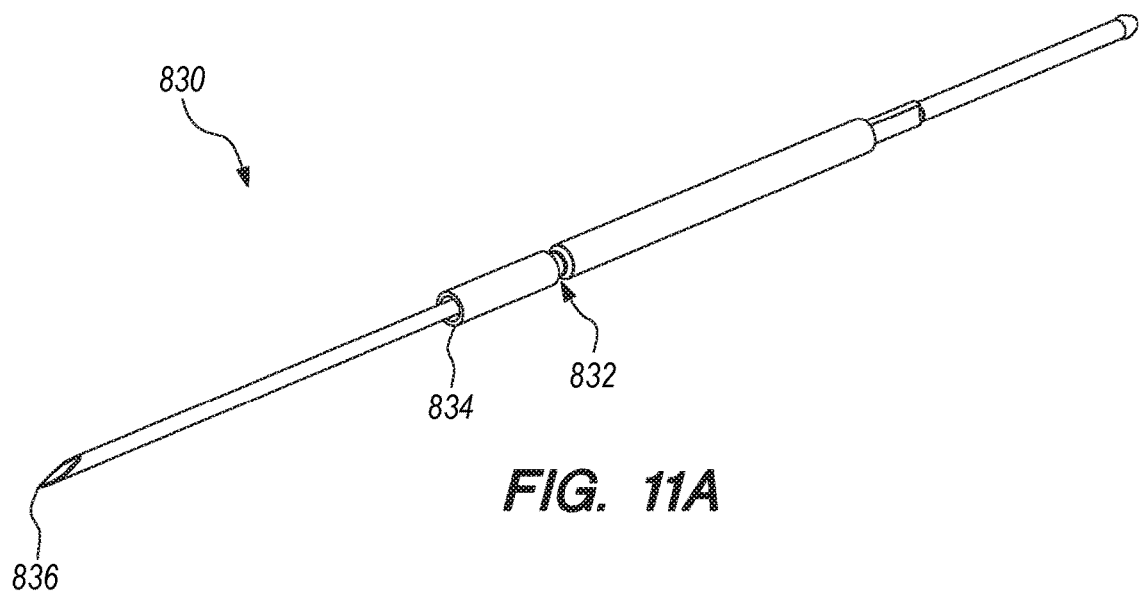
FIGS. 11A and 11B are perspective and perspective exploded views of a needle assembly according to some embodiments.
Figure 11B:
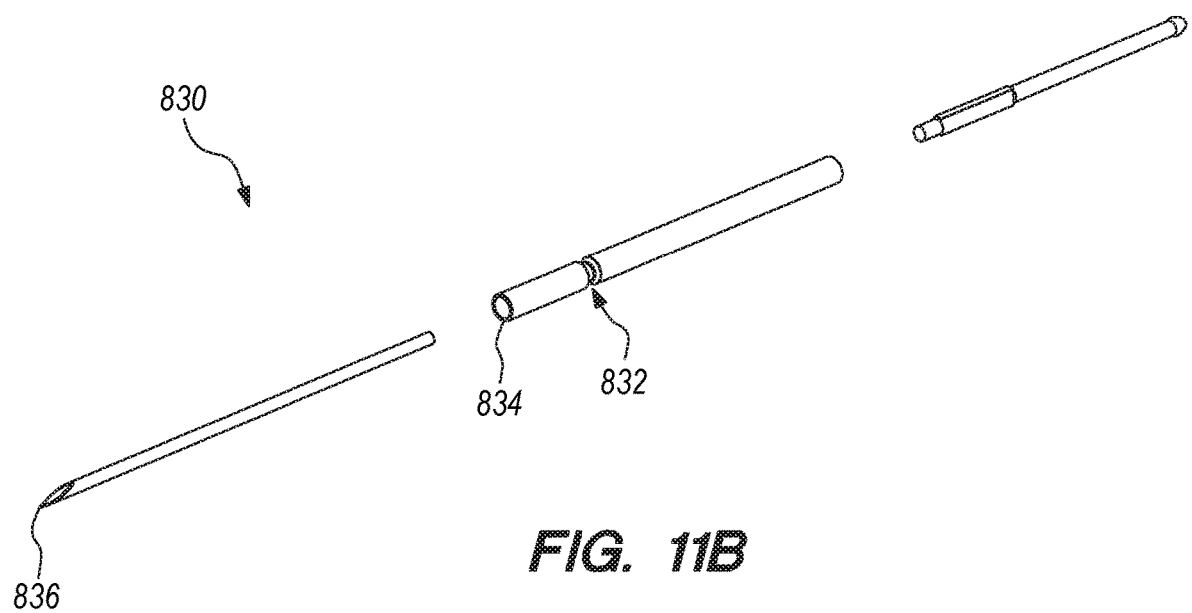

FIGS. 11A and 11B depict a needle assembly 830 according to some embodiments. The needle assembly 830 includes a notch 832 for interacting with a needle latch assembly (not shown; see FIG. 8A), a distal shoulder 834 for interacting with a proximal shoulder on an interior of a needle hub assembly 810 (not shown; see FIG. 8A), and a sharp distal end 836.

FIGS. 12A and 12B depict a needle latch assembly 840 according to some embodiments. The needle latch assembly 840 is a flat disc-shaped body. The needle latch assembly 840 includes first and second opposing deformable tabs 841, 842. The first and second opposing deformable tabs 841, 842 are asymmetric and their opposing edges partially define a smaller opening 843 located substantially in the center of the flat disc-shaped body. The needle latch assembly 840 also includes an "H" shaped opening 844 partially defined by the first and second opposing deformable tabs 841, 842.

Near the middle of one of the long legs of the "H" shaped opening 844 is formed a larger opening 845. The larger opening 845 is eccentrically located relative to the center of the flat disc-shaped body. The larger opening 845 is sized and shaped to allow passage of a needle assembly 830 (see FIG. 13A) therethrough. The smaller opening 843, on the other hand, is sized and shaped to prevent passage of a needle assembly 830 (see FIG. 14A) therethrough in a longitudinal direction. Accordingly, during manufacture/assembly as shown in FIGS. 13A to 14B, a needle assembly 830 can be inserted through the larger opening 845 (FIG. 13A) and slid into the smaller opening 843, which is sized and shaped to admit the notch 832 in the needle assembly 830 in a direction orthogonal to the longitudinal axis of the needle assembly 830. After the needle assembly 830 is slid into the smaller opening 843 from the larger opening 845, the needle assembly 830 is prevented from moving in a longitudinal direction until the first and second opposing deformable tabs 841, 842 are deformed.

The first and second opposing deformable tabs 841, 842 are configured to plastically deform when a predetermined amount of force is applied to the tabs 841, 842 in a proximal direction. In some embodiments, the predetermined amount of force is about 2 lbs. to about 3 lbs. This predetermined amount of force is almost an order or magnitude larger than the amount of force (0.25 lbs. to 0.5 lbs.) exerted on the needle assembly 830 when it punctures a patient's skin during injection. After the first and second opposing deformable tabs 841, 842 plastically deform, the needle assembly 830 is free to move longitudinally relative to the needle latch assembly 840.

The needle latch assembly 840 may be formed by stamping and/or cutting the disc-shaped body from a sheet of metal. The various openings (i.e., smaller and larger openings 843, 845, and "H" shaped opening 844) can also be stamped or cut into the disc-shaped body to form the first and second opposing deformable tabs 841, 842. Accordingly, the needle latch assembly 840 can be formed as a unitary body thereby minimizing the complexity of manufacturing/assembly.

FIGS. 15A to 15D depict a flat disc-shaped needle latch assembly 1540 according to some other embodiments. Needle latch assembly 1540 is similar to the needle latch assembly 840 depicted in FIGS. 12A and 12B. For instance, the needle latch assembly 1540 has first and second opposing deformable tabs 1541, 1542, smaller and larger openings 1543, 1545, and an "H" shaped opening 1544. A first difference is that the needle latch assembly 1540 includes a side opening 1546 on the opposite side of the disc-shaped body from the larger opening 1545. The side opening 1546 is continuous with the "H" shaped opening and an exterior of the disc-shaped body. The second difference is that the needle latch assembly 1540 includes an elastically deformable section 1547 adjacent the larger opening 1545 and opposite of the side opening 1546.

Figure 15A:
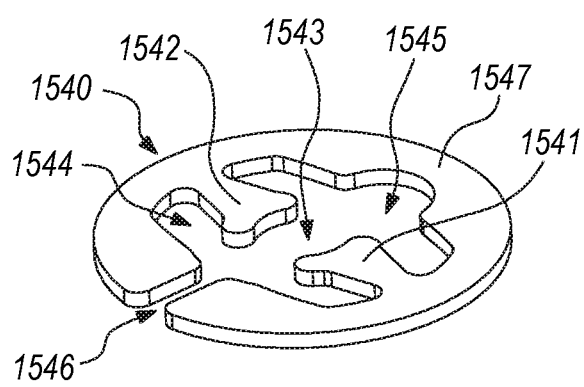
FIGS. 15A to 15D are perspective and top views of a needle latch assembly or components thereof being opened according to some embodiments.
Figure 15B:
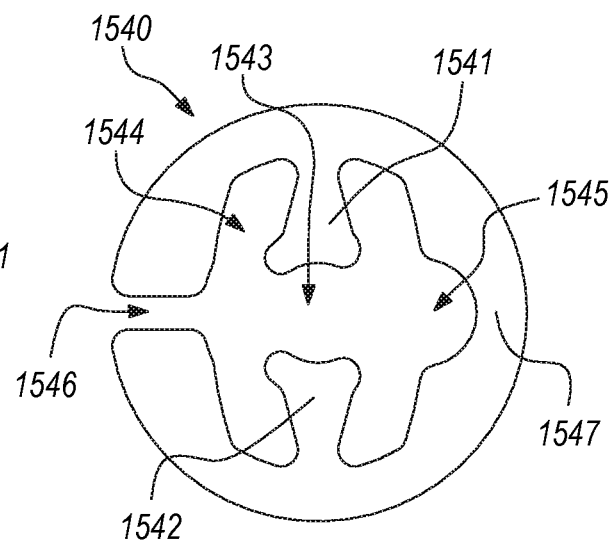
Figure 15C:
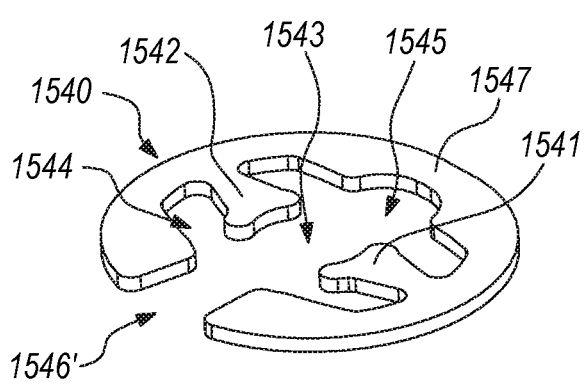
Figure 15D:
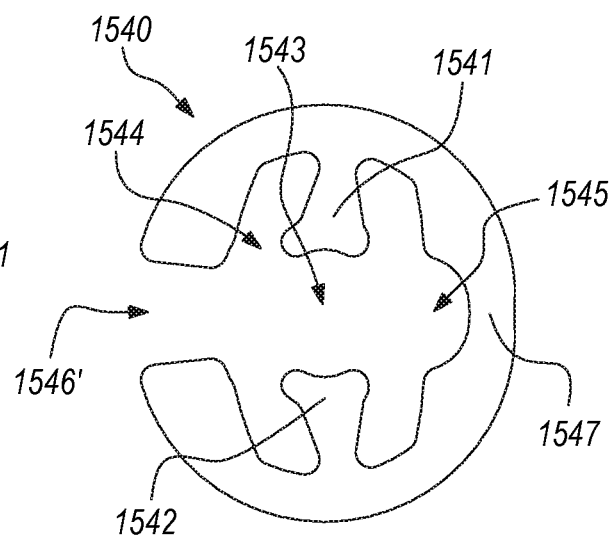

The side opening 1546 and the elastically deformable section 1547 allow the needle latch assembly 1540 to be opened by elastically deforming the elastically deformable section 1547 in the plane of the disc-shaped body to increase the size of the side opening 1546' (see FIGS. 15C and 15D). Increasing the size of the side opening 1546' allows the needle latch assembly 1540 to be slid onto a needle assembly (not shown) through the enlarged side opening 1546' during manufacture/assembly.

Figure 16A:
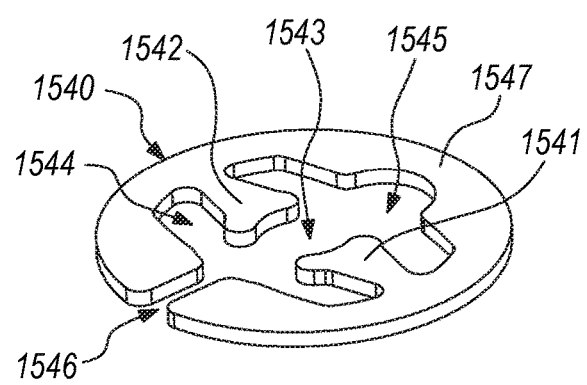
FIGS. 16A to 16D are perspective and top views of a needle latch assembly or components thereof being opened according to some embodiments.
Figure 16B:
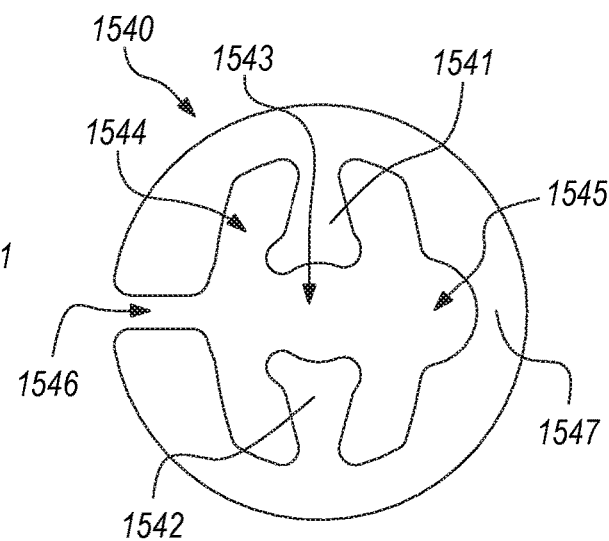
Figure 16C:
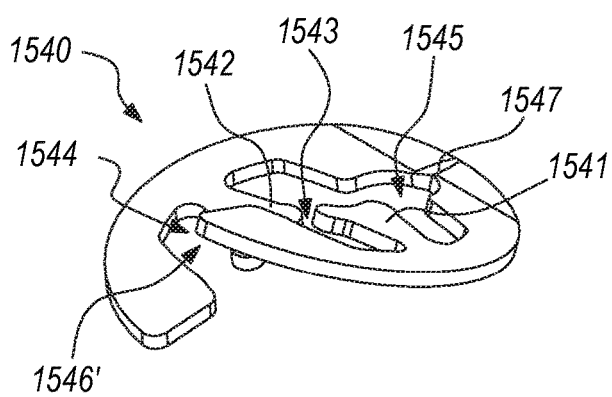
Figure 16D:
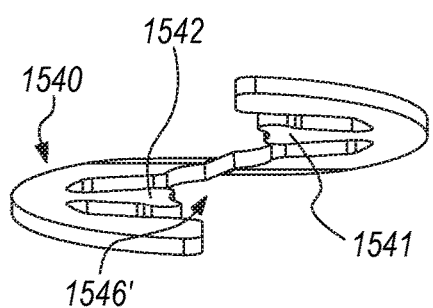
Figure 17A:
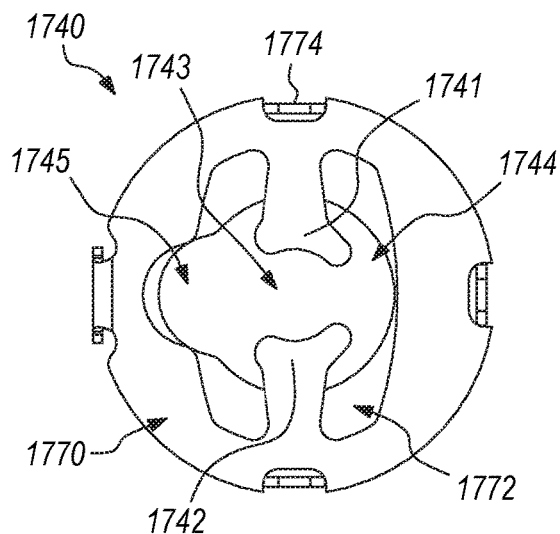
FIGS. 17A to 17D are perspective, top, and bottom views of a needle latch assembly or components thereof according to some embodiments.
Figure 17B:
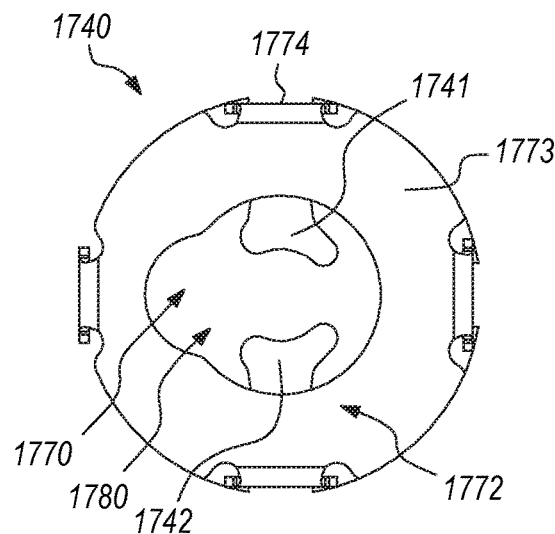
Figure 17C:
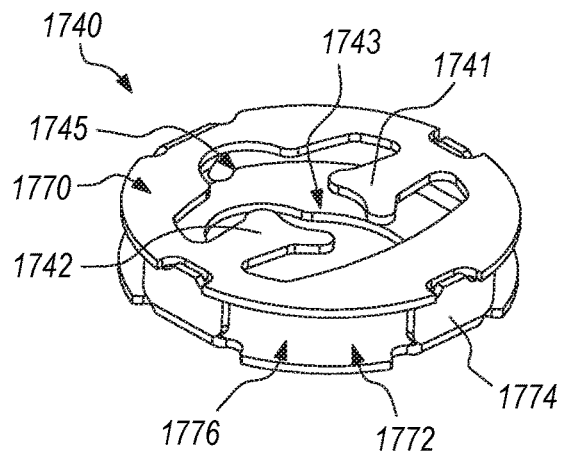
Figure 17D:
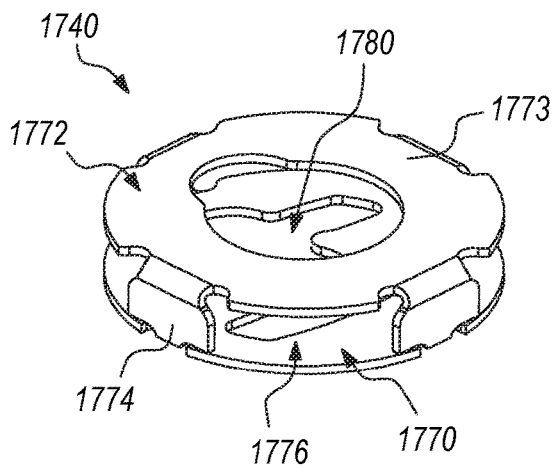

Alternatively, the needle latch assembly 1540 can be opened by elastically deforming the elastically deformable section 1547 out of the plane of the disc-shaped body to increase the size of the side opening 1546' (see FIGS. 16C and 16D). Increasing the size of the side opening 1546' allows the needle latch assembly 1540 to be slid onto a needle assembly (not shown) through the enlarged side opening 1546' during manufacture/assembly.

The needle latch assembly 1540 may be formed by stamping and/or cutting the disc-shaped body from a sheet of metal. The various openings (i.e., smaller and larger openings 1543, 1545, "H" shaped opening 1544, and side opening 1546) can also be stamped or cut into the disc-shaped body to form the first and second opposing deformable tabs 1541, 1542. Accordingly, the needle latch assembly 1540 can be formed as a unitary body thereby minimizing the complexity of manufacturing/assembly.

Exemplary 3D Disc-Shaped Needle Latch Assembly

FIGS. 17A to 21B depict a three dimensional ("3D") disc-shaped needle latch assembly 1740 and its incorporation into needle hub assemblies and safe injection systems according to various embodiments.

FIGS. 17A to 17D depict a needle latch assembly 1740 according to some embodiments. The needle latch assembly 1740 is a 3D disc-shaped needle latch assembly including a top flat disc-shaped body 1770, and a bottom flat disc-shaped body 1772, and a plurality (e.g., four) of joining members 1774 coupled to the top and bottom flat disc-shaped bodies 1770, 1772. The joining member 1774 provide a space 1776 between the top and bottom flat disc-shaped bodies 1770, 1772 such that the needle latch assembly 1740 has a 3D disc-shape. The bottom flat disc-shaped body 1772 includes a bottom facing gasket backstop surface 1773 configured to provide a flat surface for compression of the deformable sealing member/gasket 1750 (see FIGS. 19A and 19B).

The top flat disc-shaped body 1770 is identical to the needle latch assembly 840 depicted in FIGS. 12A and 12B. Accordingly, the top flat disc-shaped body 1770 is a flat disc-shaped body. The top flat disc-shaped body 1770 includes first and second opposing deformable tabs 1741, 1742. The first and second opposing deformable tabs 1741, 1742 are asymmetric and their opposing edges partially define a smaller opening 1743 located substantially in the center of the flat disc-shaped body. The top flat disc-shaped body 1770 also includes an "H" shaped opening 1744 partially defined by the first and second opposing deformable tabs 1741, 1742.

Near the middle of one of the long legs of the "H" shaped opening 1744 is formed a larger opening 1745. The larger opening 1745 is eccentrically located relative to the center of the flat disc-shaped body. The larger opening 1745 is sized and shaped to allow passage of a needle assembly (not shown) therethrough. The smaller opening 1743, on the other hand, is sized and shaped to prevent passage of a needle assembly (not shown) therethrough in a longitudinal direction.

The first and second opposing deformable tabs 1741, 1742 are configured to plastically deform when a predetermined amount of force is applied to the tabs 1741, 1742 in a proximal direction. In some embodiments, the predetermined amount of force is about 2 lbs. to about 3 lbs. This predetermined amount of force is almost an order or magnitude larger than the amount of force (0.25 lbs. to 0.5 lbs.) exerted on the needle assembly 1730 when it punctures a patient's skin during injection. After the first and second opposing deformable tabs 1741, 1742 plastically deform, the needle assembly 1730 is free to move longitudinally relative to the top flat disc-shaped body 1770.

The bottom flat disc-shaped body 1772 has an ovoid opening 1780. When the top and bottom flat disc-shaped bodies 1770, 1772 are coupled to the plurality of joining members 1774, the ovoid opening 1780 is aligned with both the smaller and larger openings 1743, 1745 defined in the top flat disc-shaped body 1770. Accordingly, the ovoid opening 1780 defined in the bottom flat disc-shaped body 1772 allows a needle assembly (not shown) to be inserted through the needle latch assembly 1740.

Figure 18A:
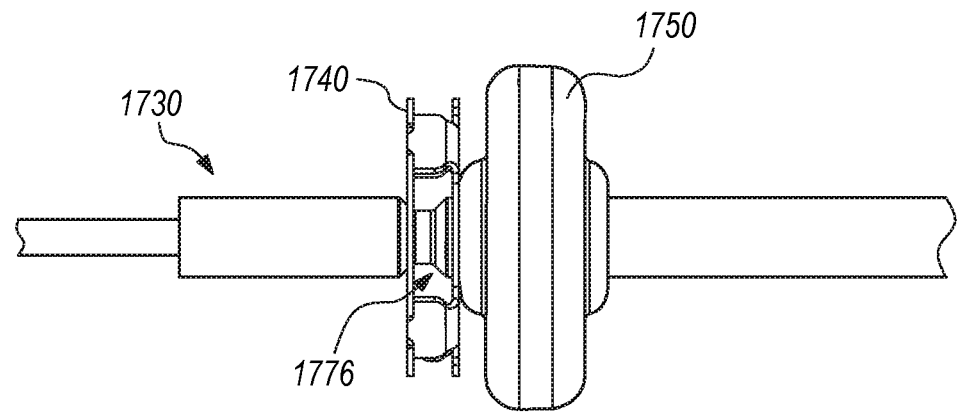
FIGS. 18A and 18B are side and perspective views of a needle latch assembly or components thereof mounted on a needle assembly according to some embodiments.
Figure 18B:
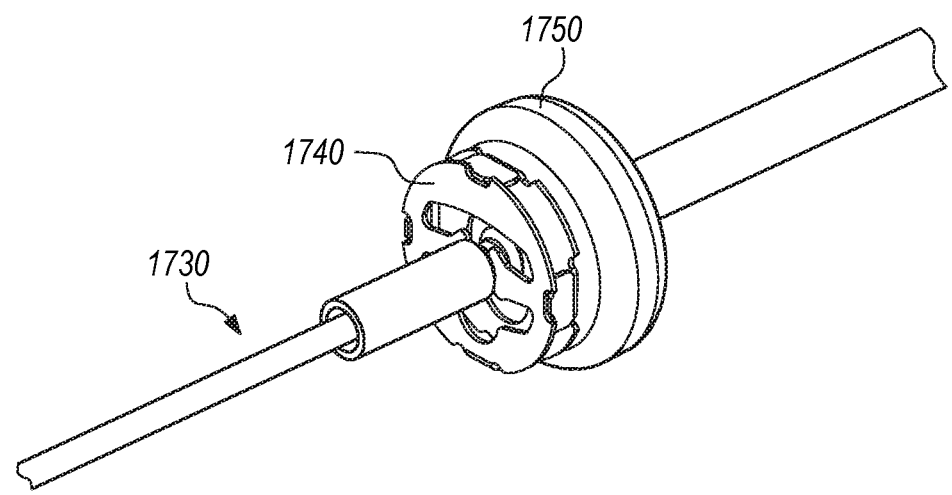

FIGS. 18A and 18B depict the needle latch assembly 1740 mounted on a needle assembly 1730 with a deformable sealing member/gasket 1750 on a proximal side thereof. As shown in FIG. 18A, the space 1776 created by the plurality of joining members 1774 prevents the deformable sealing member 1750 from making contact with the top flat disc-shaped body 1770. Accordingly, the sealing member 1750 does not interfere with plastic deformation of the first and second opposing deformable tabs 1741, 1742 in the top flat disc-shaped body 1770.

Figure 19A:
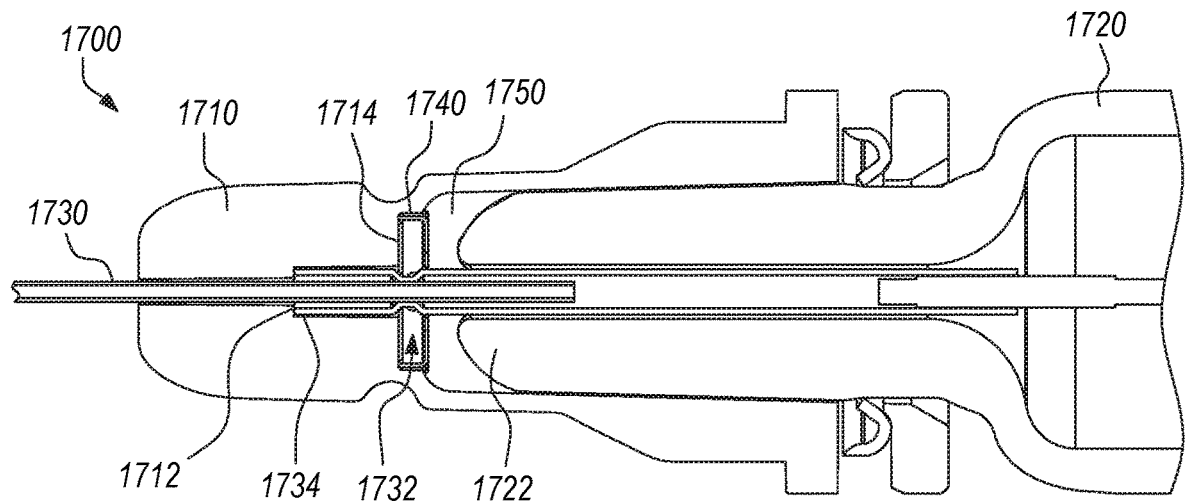
FIGS. 19A and 19B are longitudinal cross-sectional and perspective cut away views of a safe injection system according to some embodiments.
Figure 19B:
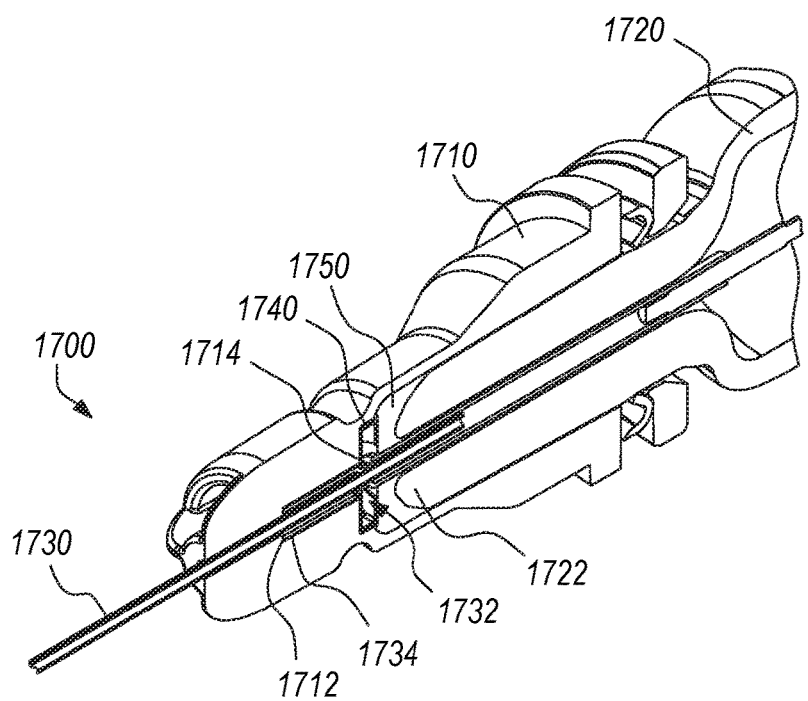

FIGS. 19A and 19B depict a safe injection system 1700 according to some embodiments. FIGS. 19A and 19B depict a safe injection system 1700 in an assembled and ready to use configuration. FIGS. 19A and 19B provide similar views to FIGS. 8A and 8B, and similar components are labeled with corresponding reference numerals. One difference between the two safe injection systems 1700, 800 is that the safe injection systems 1700 includes the 3D needle latch assembly 1740 and therefore includes a larger space inside of the needle hub assembly 1710 to accommodate the larger 3D needle latch assembly 1740.

Figure 20A:
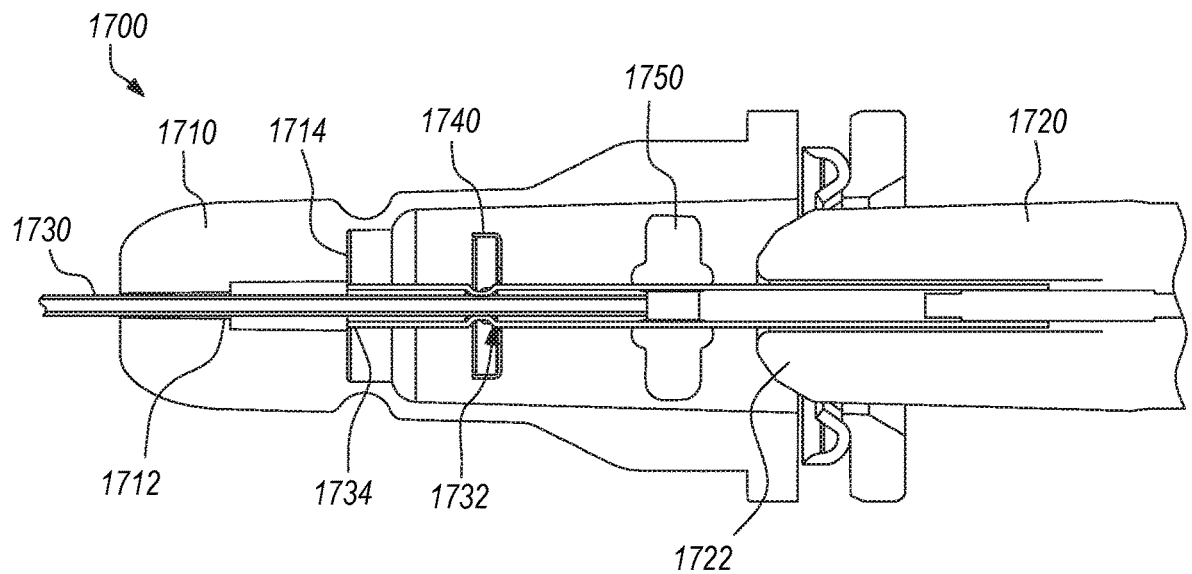
FIGS. 20A and 20B are longitudinal cross-sectional and perspective cut away exploded views of a safe injection system according to some embodiments.
Figure 20B:
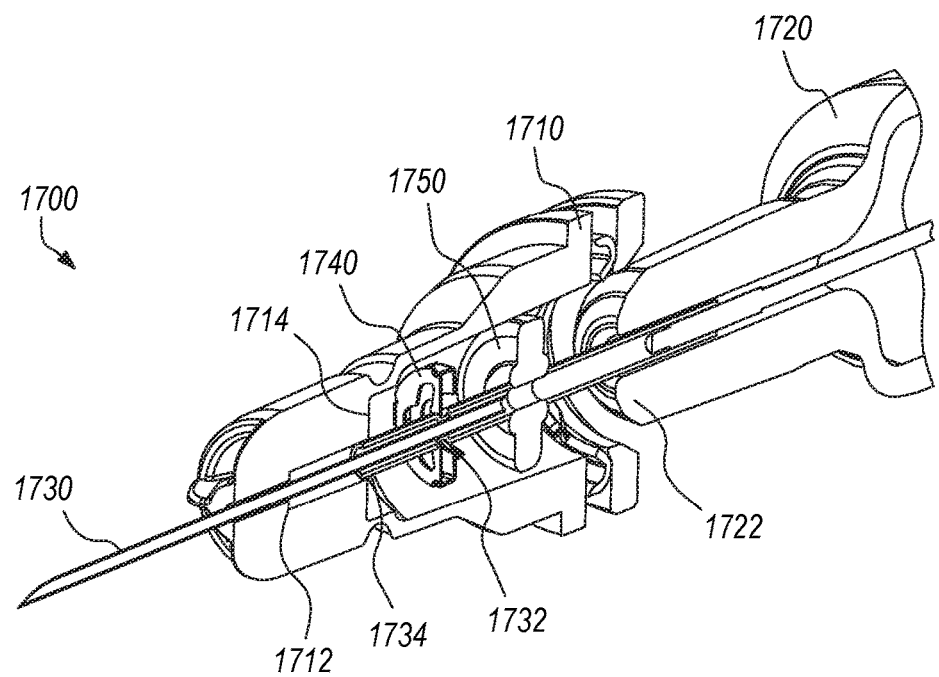
Figure 21A:
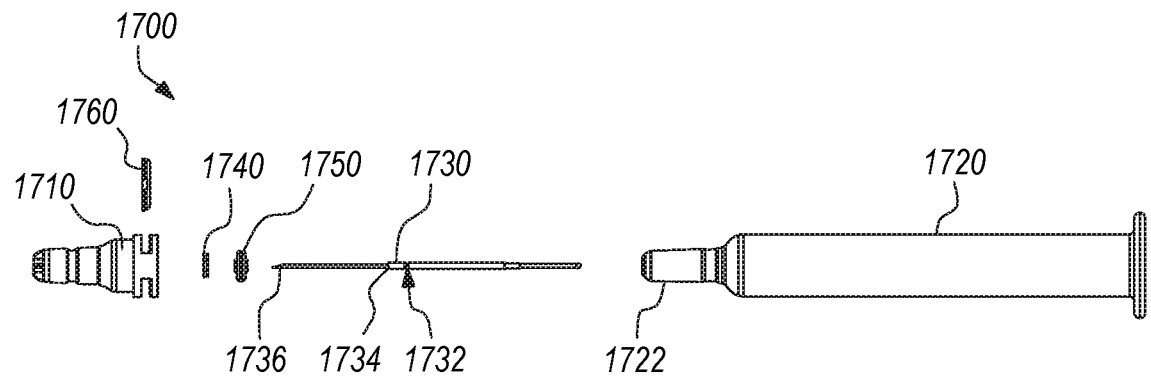
FIGS. 21A and 21B are side and perspective exploded views of components of a safe injection system according to some embodiments.
Figure 21B:
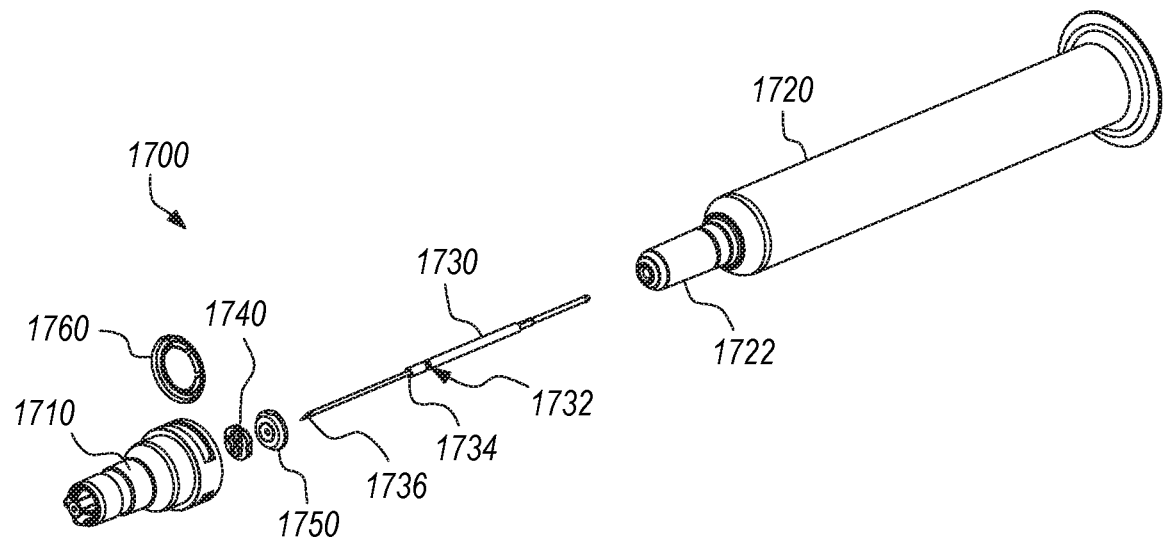

FIGS. 20A and 20B depict the safe injection system 1700 in two exploded views similar to FIGS. 9A and 9B, and similar components are labeled with corresponding reference numerals. FIGS. 21A and 21B depict the safe injection system 1700 in two further exploded views similar to FIGS. 10A and 10B, and similar components are labeled with corresponding reference numerals. The difference between the safe injection systems 1700, 800 is the 3D needle latch assembly 1740 in safe injection system 1700 compared to the flat needle latch assembly 840 in safe injection system 800. The 3D needle latch assembly 1740 requires more space in the needle hub assembly 1710 in the safe injection system 1700. However, the 3D needle latch assembly 1740 provides more consistency in unlatching because the space 1776 in the 3D needle latch assembly 1740 prevents the sealing member 1750 from interfering with plastic deformation of the first and second opposing deformable tabs 1741, 1742 in the top flat disc-shaped body 1770.

FIGS. 20A to 21B depict the deformable sealing member 1750 in an uncompressed/relaxed state. FIGS. 19A and 19B depict the deformable sealing member 1750 in a compressed/biased state.

The needle latch assembly 1740 may be formed by stamping and/or cutting the top and bottom disc-shaped bodies 1770, 1772 and the joining members 1774 from a sheet of metal. Then the top and bottom disc-shaped bodies 1770, 1772 and the joining members 1774 are folded and joined (e.g., welded) to form the 3D needle latch assembly 1740. The various openings (i.e., smaller and larger openings 1743, 1745 and "H" shaped opening 1744) can also be stamped or cut into the top disc-shaped body to form the first and second opposing deformable tabs 1741, 1742. The ovoid opening 1780 can further be stamped or cut into the bottom disc-shaped body. Accordingly, the needle latch assembly 1740 can be formed as a unitary body thereby minimizing the complexity of manufacturing/assembly.

Exemplary Needle Latch Assembly with Collar

Figure 22A:
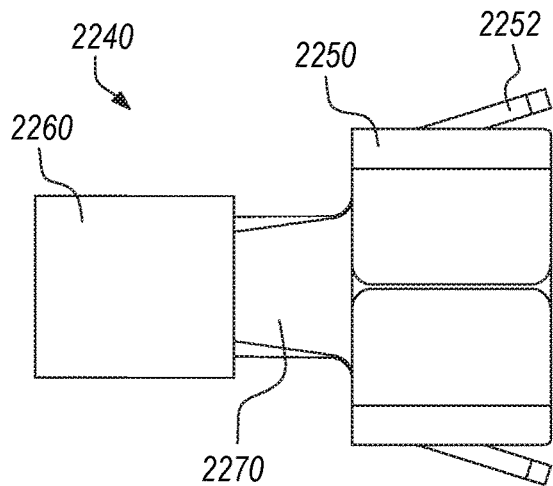
FIGS. 22A, 22B, and 22C are top, front, and perspective views of a needle latch assembly or components thereof according to some embodiments.
Figure 22B:
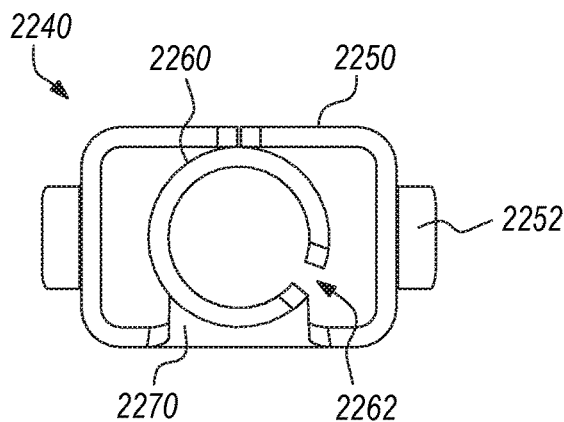
Figure 22C:
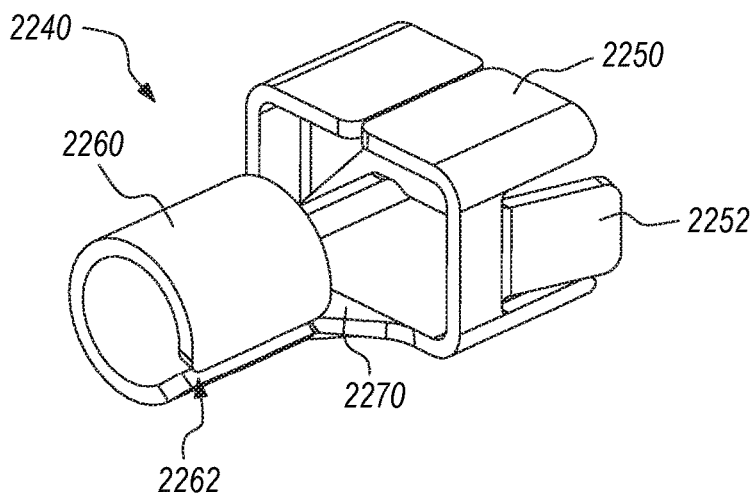

FIGS. 22A to 22C depict a 3D needle latch assembly 2240 with a needle collar 2260 according to various embodiments. The needle latch assembly 2240 includes a rectangular prism retaining portion 2250, a cylindrical needle collar portion 2260, and a joining portion 2270 coupling the cylindrical needle collar portion 2260 to the rectangular prism retaining portion 2250.

The rectangular prism retaining portion 2250 is sized and shaped to be securely disposed in a chamber defined in a needle hub assembly (not shown). The rectangular prism retaining portion 2250 also includes a pair of outwardly biased tabs 2252 that allow the retaining portion 2250 to be inserted into the chamber in the needle hub assembly, but prevents the retaining portion 2250 from being removed from the chamber in the needle hub assembly. The rectangular prism retaining portion 2250 is a rectangular box formed by folding two right angles into each of two ends of a strip (e.g., metal) until the free ends of the strip meet, thereby forming a rectangular box.

Figure 23A:
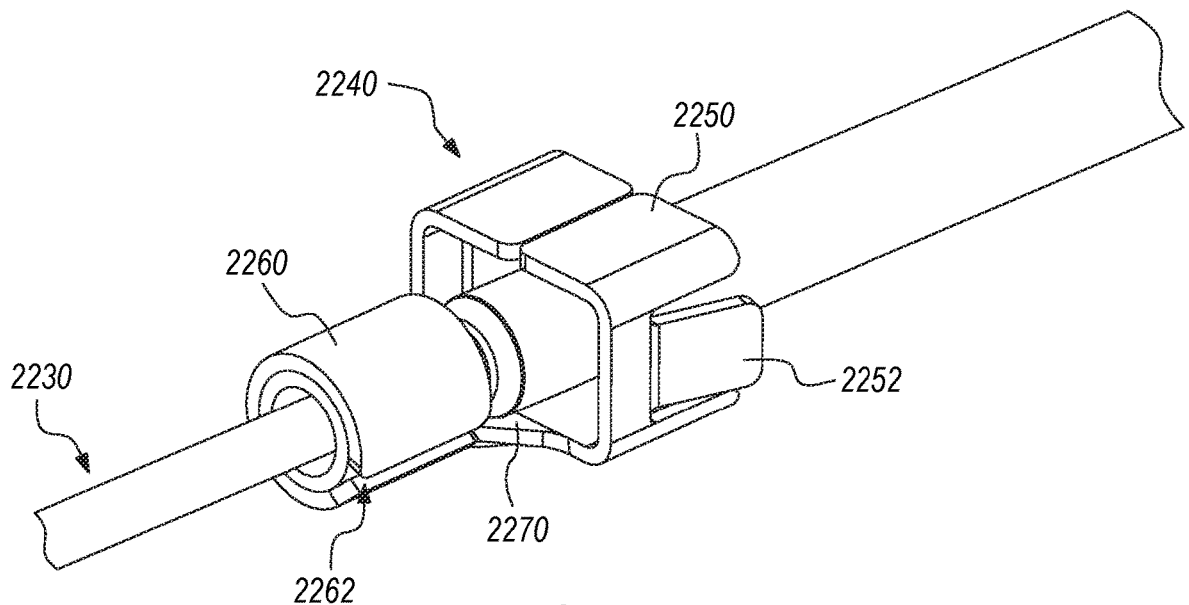
FIGS. 23A and 23B are perspective views of a needle latch assembly or components thereof latched to and unlatched from a needle assembly according to some embodiments.
Figure 23B:
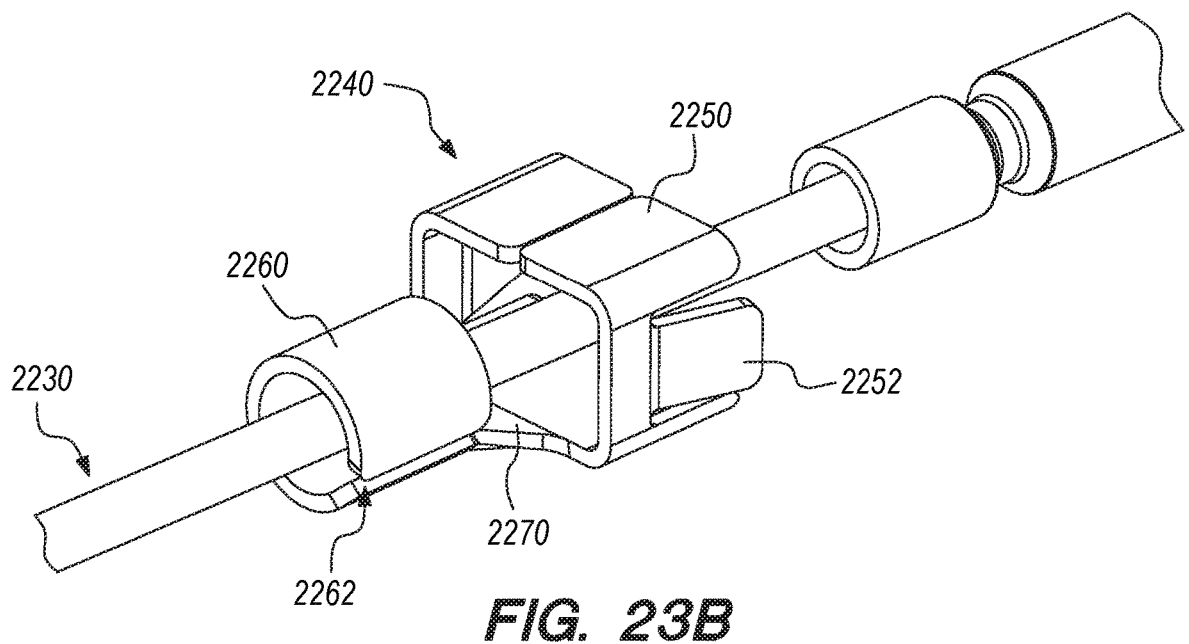

The cylindrical needle collar portion 2260 is formed by rolling a sheet (e.g., metal) until two free ends of the sheet almost meet, thereby forming a cylinder with a longitudinal opening 2262. The cylindrical needle collar portion 2260 is plastically deformable. Accordingly, the cylindrical needle collar portion 2260 can be opened plastically at the longitudinal opening 2262 and crimped onto a needle assembly 2230 (FIG. 23A). When the cylindrical needle collar portion 2260 is crimped onto/coupled to a needle assembly 2230, the needle assembly 2230 is restrained from moving longitudinally relative to the needle latch assembly 2240. Applying a predetermined amount of proximally directed force to the cylindrical needle collar portion 2260 (via the needle assembly 2230) plastically deforms the cylindrical needle collar portion 2260 by enlarging the longitudinal opening 2262 and releasing the needle assembly 2230 from the needle latch assembly 2240 (FIG. 23B). In some embodiments, the proximally directed force is from about 2 lbs. to about 3 lbs. While FIGS. 23A and 23B depict a needle assembly 2230 with a notch, the needle latch assembly 2240 will work equally well with needle assemblies without notches.

The needle latch assembly 2240 may be formed by stamping and/or cutting the rectangular prism retaining portion 2250, the cylindrical needle collar portion 2260, and the joining members 2270 from a sheet of metal. Then various components of the rectangular prism retaining portion 2250, the cylindrical needle collar portion 2260, and the joining members 2270 are folded and joined (e.g., welded) as needed to form the needle latch assembly 2240. Accordingly, the needle latch assembly 2240 can be formed as a unitary body thereby minimizing the complexity of manufacturing/assembly.

Exemplary Three Dimensional Needle Latch Assembly with Floating Tabs

FIGS. 24A to 28B depict a 3D needle latch assembly 2440 with "floating tabs" 2441 and its incorporation into needle hub assemblies and safe injection systems according to various embodiments.

FIGS. 24A to 24D depict a needle latch assembly 2440 according to some embodiments. The needle latch assembly 2440 is a 3D needle latch assembly including a flat rectangular-shaped body 2472, first and second arms 2474, and first and second pairs of standoffs 2470 formed on respective opposite ends of the first and second arms 2474 from the flat rectangular-shaped body 2472. The flat rectangular-shaped body 2472, first and second arms 2474, and first and second pairs of standoffs 2470 define a cage with the flat rectangular-shaped body 2472 and the first and second pairs of standoffs 2470 at opposite ends thereof. The first and second arms 2474 have respective arcuate axial cross-sections that bend toward each other, such that the first and second arms 2474 form portions of a cylinder so that the needle latch assembly 2440 is rotatable when disposed in a corresponding round chamber (see FIGS. 26A and 26B).

Figure 26A:
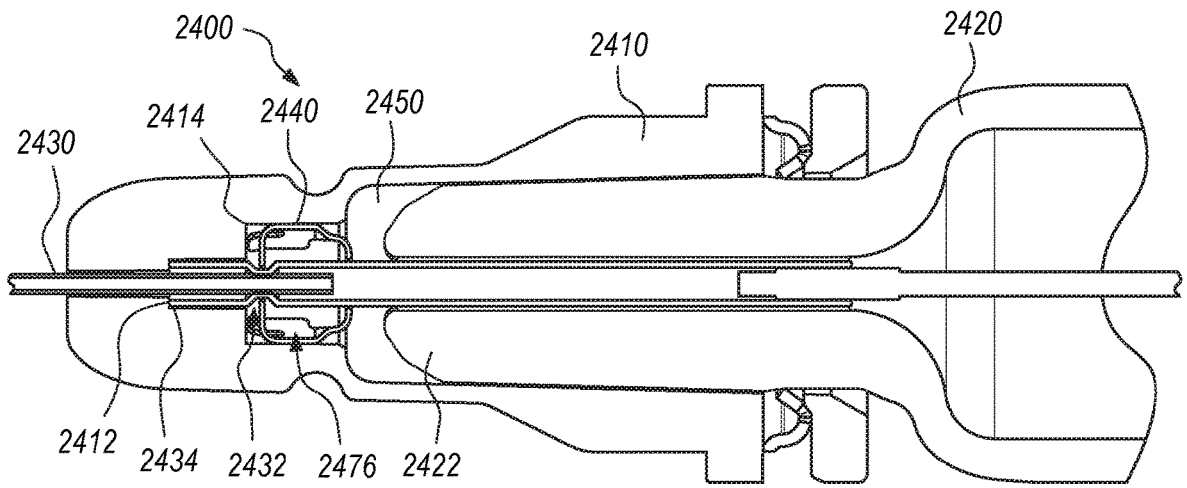
FIGS. 26A and 26B are longitudinal cross-sectional and perspective cut away views of a safe injection system according to some embodiments.
Figure 26B:
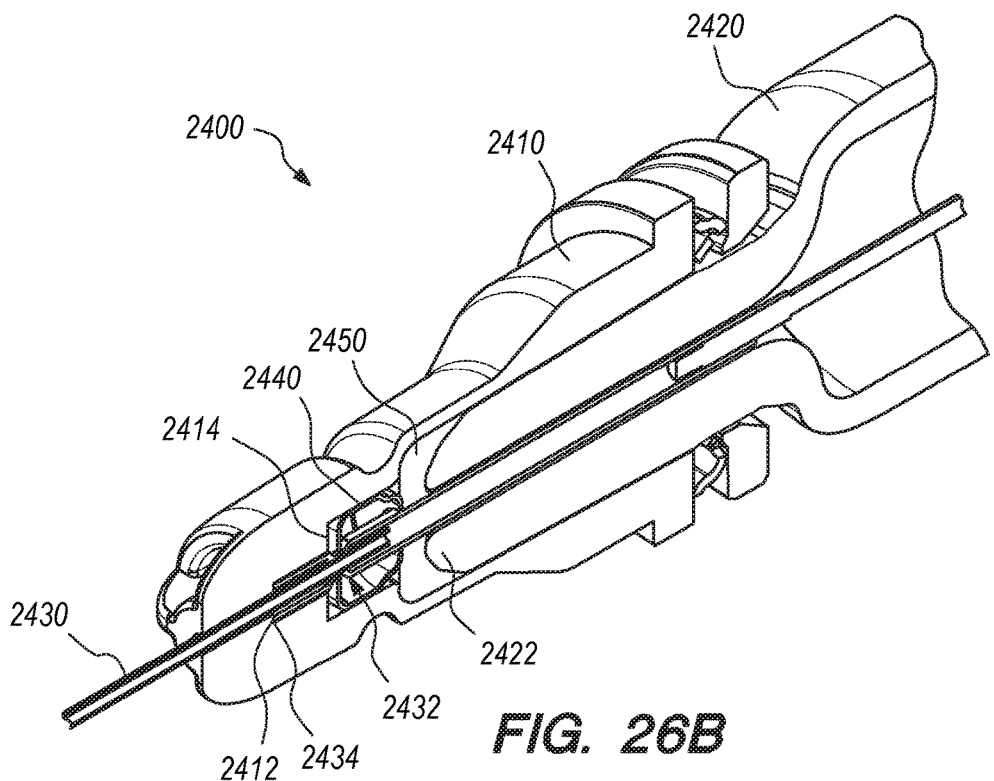
Figure 27A:
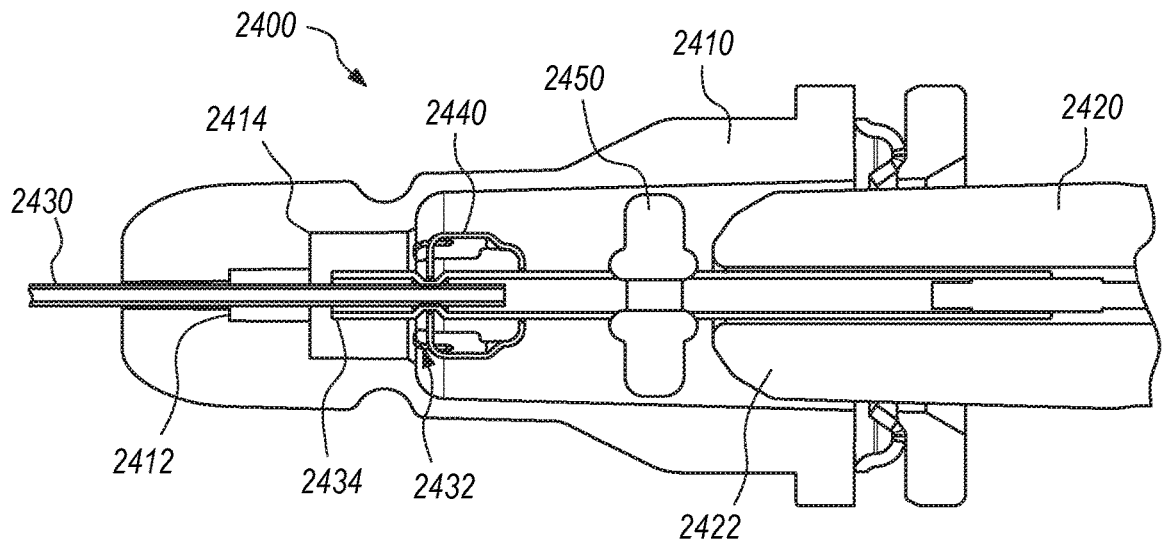
FIGS. 27A and 27B are longitudinal cross-sectional and perspective cut away exploded views of a safe injection system according to some embodiments.
Figure 27B:
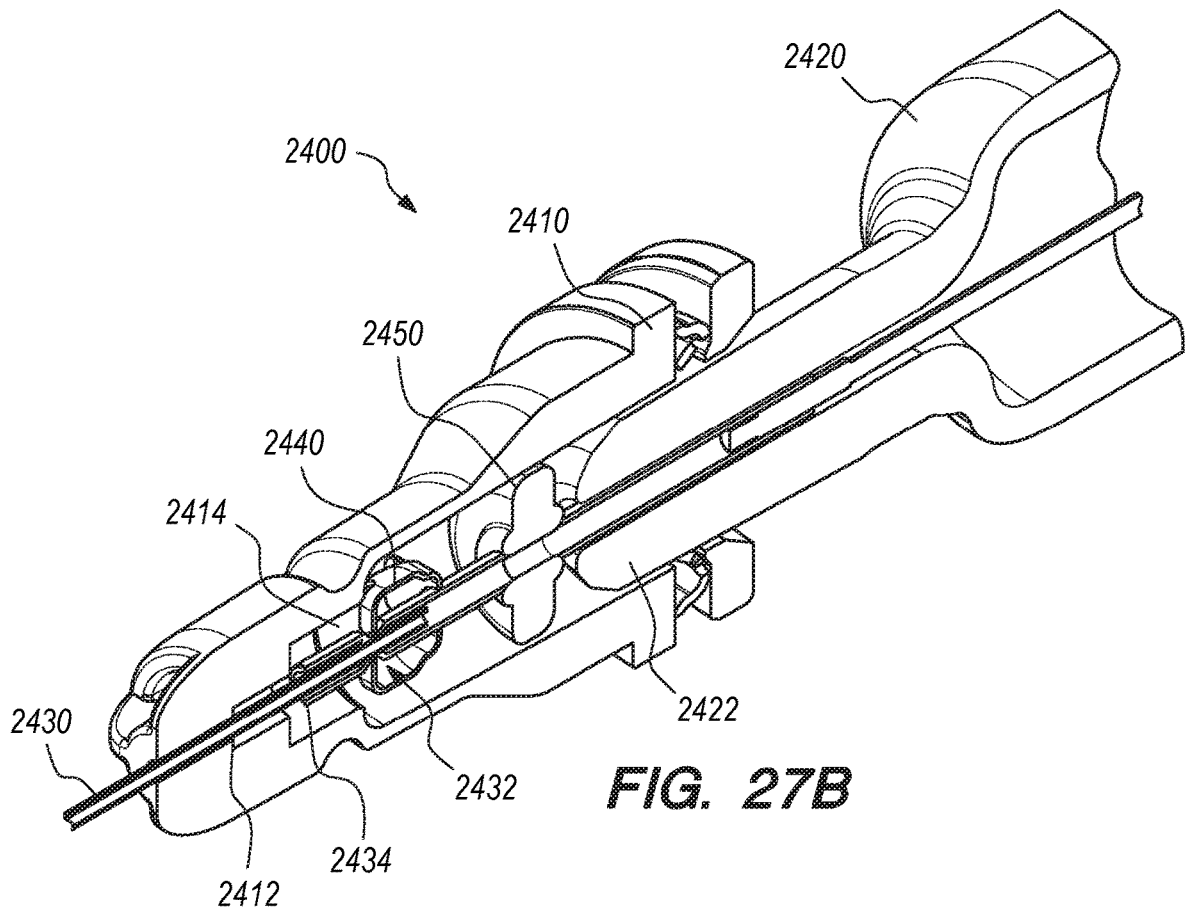

The flat rectangular-shaped body 2472 may be configured to interfere with an internal shoulder in the needle hub assembly 2410 (see FIGS. 26A and 26B) to limit distal movement of the needle latch assembly 2440 relative to the needle hub assembly 2410. The flat rectangular-shaped body 2472 is also a bottom facing gasket backstop surface 2473 configured to provide a flat surface for compression of the deformable sealing member/gasket 2450 (see FIGS. 26A and 26B). As shown in FIGS. 27A and 27B, the needle assembly 2430 includes a distal shoulder 2434 that interferes with a proximal shoulder 2412 formed on an interior surface of the needle hub assembly 2410 to also limit distal movement of the needle assembly 2430 relative to the needle hub assembly 2410. FIGS. 26A and 26B illustrates the distal shoulder 2434 of the needle assembly 2430 abutting the proximal shoulder 2412 of the needle hub assembly 2410 to limit distal movement of the needle assembly 2430 relative to the needle hub assembly 2410.

The first and second arms 2474 are orthogonal to the plane of the flat rectangular-shaped body 2472. The respective hinges formed where the first and second arms 2474 are coupled to the plane of the flat rectangular-shaped body 2472 are elastically deformable. Consequently, when the needle latch assembly 2440 disposed in a corresponding round chamber (see FIGS. 26A and 26B) with a slightly smaller diameter than the diameter of the needle latch assembly 2440, the first and second arms 2474 may be biased radially outward to hold the needle latch assembly 2440 in the round chamber. Also, the first and second arms 2474 can open to allow insertion of the needle assembly 2430 through the smaller opening 2443 defined thereby during assembly. After assembly, the round chamber prevents opening of the first and second arms 2474.

The first and second arms 2474 are elastically deformable in the pre-assembly state, but not in the assembled state. As such, the first and second arms 2474 elastically deform to open the smaller opening 2443 when the needle latch assembly 2440 is mounted on the needle assembly 2430 during assembly of the safe injection system 2400. After the injection is completed, the first and second arms 2474 cannot deform to release the needle assembly 2440. However, with sufficient proximally directed retraction force applied, the first and second tabs 2441 are free to deform plastically to release the needle latch assembly 2440 from the needle latch assembly 2440, as described herein for retraction of the needle assembly 2430 into the syringe body 2420.

Figure 24A:
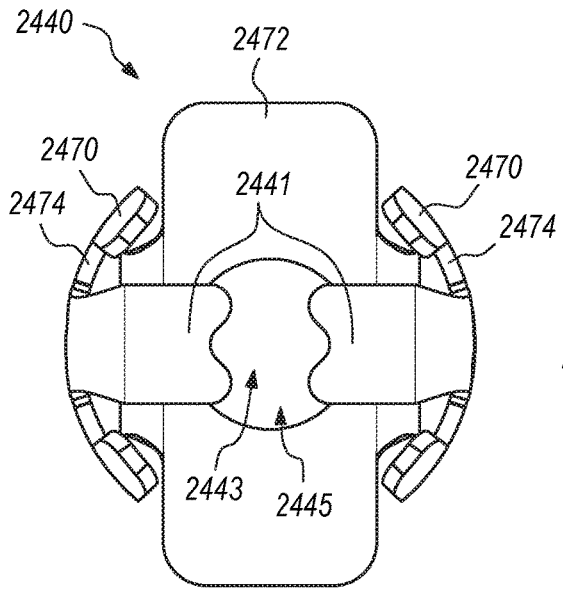
FIGS. 24A to 24D are perspective, top, and bottom views of a needle latch assembly or components thereof according to some embodiments.
Figure 24B:
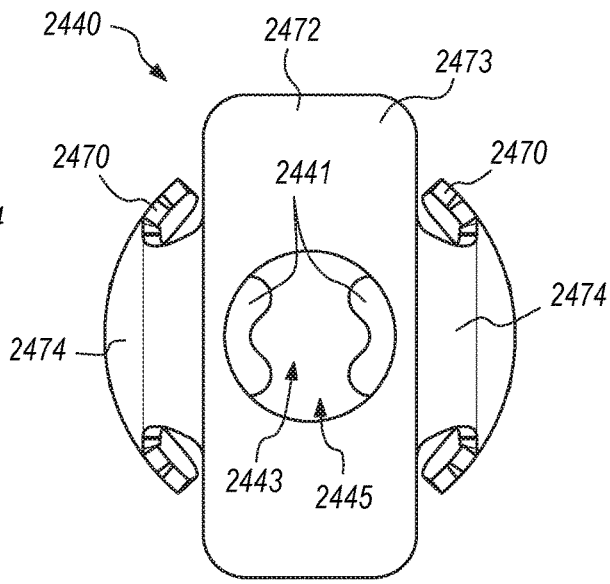
Figure 24C:
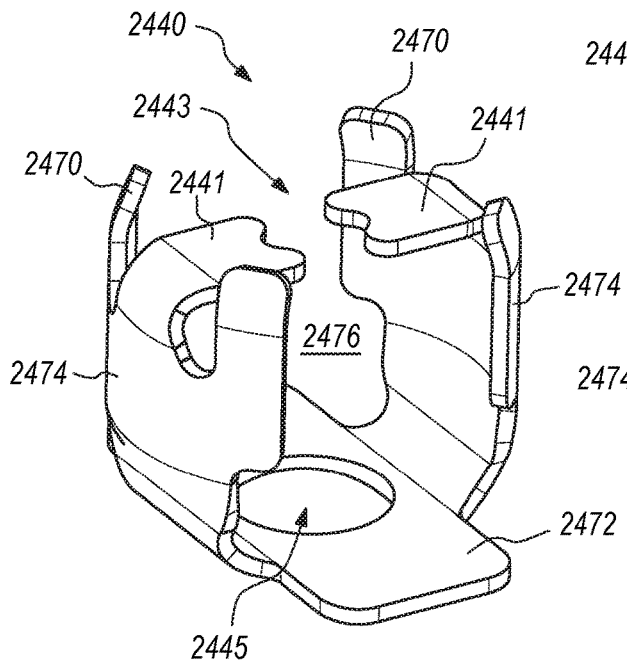
Figure 24D:
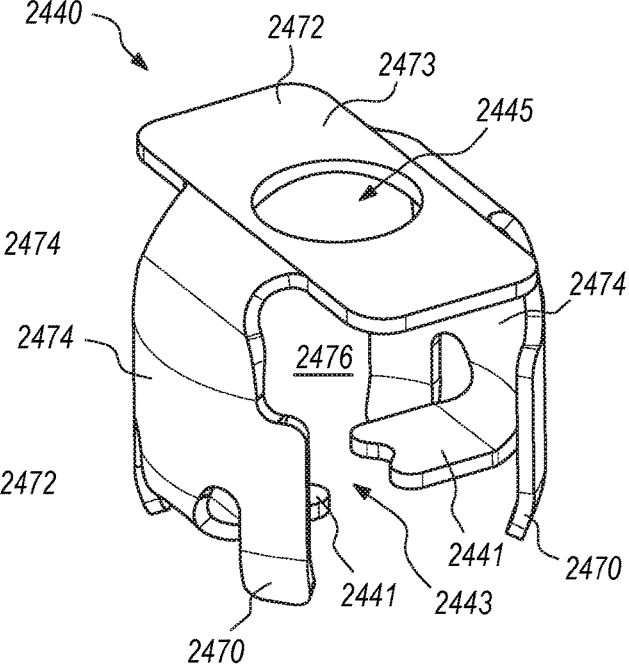

As shown in FIG. 24C, first and second tabs 2441 extend orthogonally toward each other from the first and second arms 2474 respectively. The first and second tabs 2441 are substantially symmetrical and their opposing edges partially define a smaller opening 2443 located substantially in the center of a plane in which the first and second tabs 2441 extend toward each other. The flat rectangular-shaped body 2472 defines a larger opening 2445 substantially in the center thereof. The smaller and larger openings are substantially coaxial/aligned along an axis of a needle assembly 2430 on which the needle latch assembly 2440 is mounted (see FIGS. 26A and 26B).

The first and second tabs 2441 are configured to plastically deform when a predetermined amount of force is applied to the tabs 2441 in a proximal direction. In some embodiments, the predetermined amount of force is about 2 lbs. to about 3 lbs. This predetermined amount of force is almost an order or magnitude larger than the amount of force (0.25 lbs. to 0.5 lbs.) exerted on the needle assembly 2430 when it punctures a patient's skin during injection. After the first and second tabs 2441 plastically deform, the needle assembly 2430 is free to move longitudinally relative to the needle latch assembly 2440.

As shown in FIGS. 24C and 27A, the first and second pairs of standoffs 2470 are bent toward each other. As such, the standoffs 2470 guide the needle latch assembly 2440 into the chamfered opening to the chamber formed in the needle hub assembly 2410 during assembly of the safe injection system 2400.

As described above, the flat rectangular-shaped body 2472, first and second arms 2474, and first and second pairs of standoffs 2470 define a cage with the flat rectangular-shaped body 2472 and the first and second pairs of standoffs 2470 at opposite ends thereof. As shown in FIG. 24C, the first and second tabs 2441 extend orthogonally from respective first and second arms 2470 between the flat rectangular-shaped body 2472 and the first and second pairs of standoffs 2470 in a space 2476 defined by the cage. Therefore, the first and second tabs 2441 are configured to engage with and disengage from a needle assembly 2430 while remaining inside of the cage (see FIGS. 26A and 26B). Because the first and second tabs 2441 are disposed in the space 2476, they are called "floating tabs." As such, the interior of the needle hub assembly 2410 and the deformable sealing member 2450 will not interfere with the first and second tabs 2441 and their interactions with the needle assembly 2430. Protecting the floating tabs 2441 inside of the cage allows the needle retention force to be independent of force applied to the needle latch assembly 2440 during assembly of the safe injection system 2400, which is often variable. Protecting floating tabs 2441 inside of the cage also allows the needle retention force to be independent of the geometry of the deformable sealing member 2450, as well as the tolerances of the various parts in the assembly. In effect, the cage formed by the flat rectangular-shaped body 2472, first and second arms 2474, and first and second pairs of standoffs 2470 react out/absorb the compression force from the needle hub assembly 2410 and the deformable sealing member 2450 during assembly.

Figure 25A:
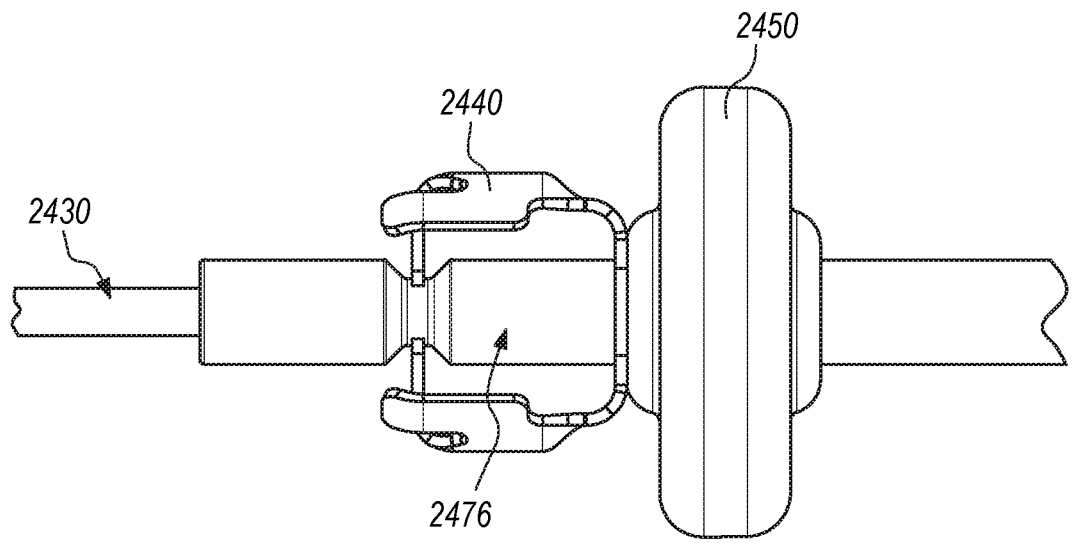
FIGS. 25A and 25B are side and perspective views of a needle latch assembly or components thereof mounted on a needle assembly according to some embodiments.
Figure 25B:
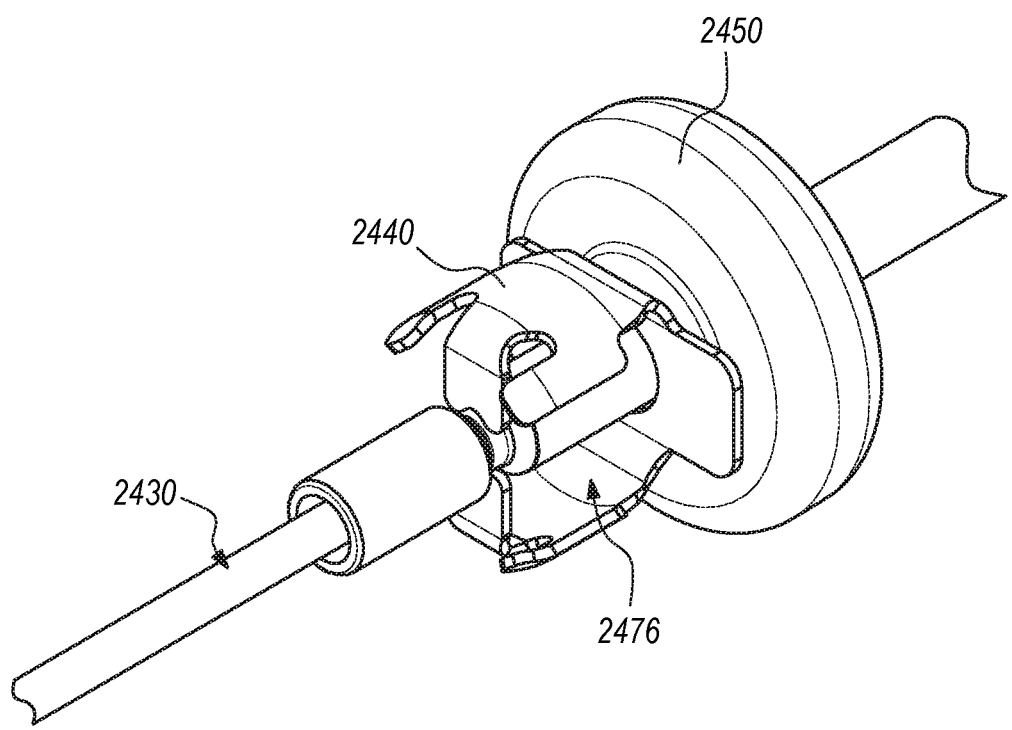

FIGS. 25A and 25B depict the needle latch assembly 2440 mounted on a needle assembly 2430 with a deformable sealing member 2450 on a proximal side thereof. As shown in FIG. 25A, the space 2476 in the cage prevents the deformable sealing member 2450 from making contact with the first and second tabs 2441. Accordingly, the sealing member 2450 does not interfere with plastic deformation of the first and second tabs 2441.

FIGS. 26A and 26B depict a safe injection system 2400 according to some embodiments. FIGS. 26A and 26B depict a safe injection system 2400 in an assembled and ready to use configuration. FIGS. 26A and 26B provide similar views to FIGS. 8A and 8B, and similar components are labeled with corresponding reference numerals. One difference between the two safe injection systems 2400, 800 is that the safe injection system 2400 includes the 3D needle latch assembly 2440 and therefore includes a larger chamber inside of the needle hub assembly 2410 to accommodate the larger 3D needle latch assembly 2440.

As shown in FIG. 26A, the space 2476 in the cage prevents the proximal interior wall 2414 of the needle hub assembly 2410 from making contact with the first and second tabs 2441. Accordingly, the needle hub assembly 2410 does not interfere with plastic deformation of the first and second tabs 2441.

Figure 28A:
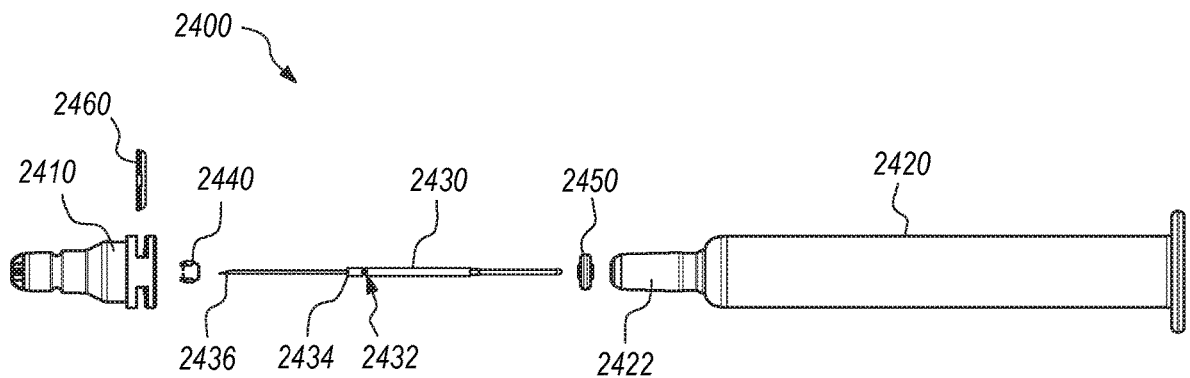
FIGS. 28A and 28B are side and perspective exploded views of components of a safe injection system according to some embodiments.
Figure 28B:
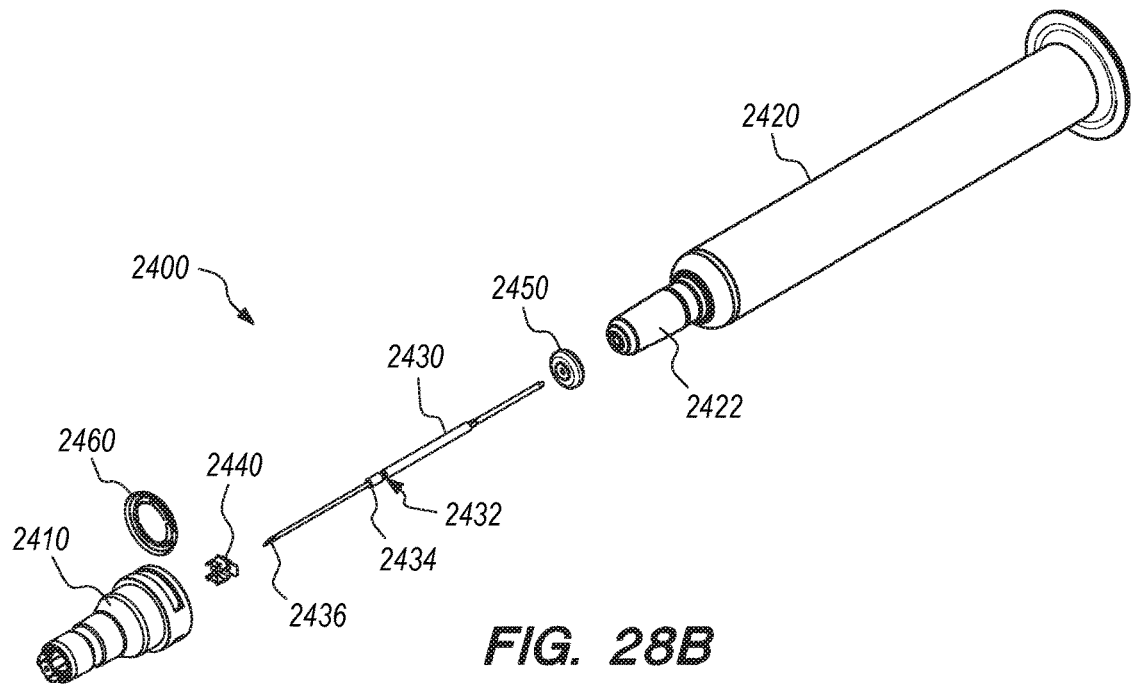

FIGS. 27A and 27B depict the safe injection system 2400 in two exploded views similar to FIGS. 9A and 9B, and similar components are labeled with corresponding reference numerals. FIGS. 28A and 28B depict the safe injection system 2400 in two further exploded views similar to FIGS. 10A and 10B, and similar components are labeled with corresponding reference numerals. The difference between the safe injection systems 2400, 800 is the 3D needle latch assembly 2440 in safe injection system 2400 compared to the flat needle latch assembly 840 in safe injection system 800. The 3D needle latch assembly 2440 requires a larger chamber in the needle hub assembly 2410 in the safe injection system 2400. However, the 3D needle latch assembly 2440 provides more consistency in unlatching because the space 2476 in the 3-D needle latch assembly 2440 prevents the sealing member 2450 and the needle hub assembly 2410 from interfering with plastic deformation of the first and second tabs 2441 in the top flat disc-shaped body 2470.

FIGS. 27A to 28B depict the deformable sealing member 2450 in an uncompressed/relaxed state. FIGS. 26A and 26B depict the deformable sealing member 2450 in a compressed/biased state.

The needle latch assembly 2440 may be formed by stamping and/or cutting the flat rectangular-shaped body 2472, first and second arms 2474, first and second pairs of standoffs 2470, and first and second tabs 2441 from a sheet of metal. Then the first and second tabs 2441, the first and second pairs of standoffs 2470, and the first and second arms are folded/bent to form the 3D needle latch assembly 2440. The smaller and larger openings 2443, 2445 can also be stamped or cut into the flat rectangular-shaped body 2472. Accordingly, the needle latch assembly 2440 can be formed as a unitary body thereby minimizing the complexity of manufacturing/assembly.

The needle latch assemblies 840, 1540, 1740, 2240 disclosed herein can all be stamped and/or cut from a sheet of metal and folded and/or joined (e.g., welded) as needed to form the needle latch assemblies 840, 1540, 1740, 2240. This minimizes the complexity of manufacturing/assembly and renders the manufacturing/assembly process more amenable to automation. The needle latch assemblies 840, 1540, 1740, 2240 are configured to unlatch with the application of 2 lbs. to 3 lbs. of proximally directed force thereto, which is almost an order or magnitude larger than the amount of force (0.25 lbs. to 0.5 lbs.) exerted on the needle assembly 830 when it punctures a patient's skin during injection. The needle latch assemblies 840, 1540, 1740, 2240 also reduce the number of parts, thereby increasing the consistency of needle unlatching to provide more consistent needle retraction safe injection systems and methods.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A syringe assembly, comprising:
   a syringe body having a syringe interior, a longitudinal axis, proximal and distal ends, and a needle attachment interface disposed at the distal end thereof;
   a needle assembly having proximal and distal ends;
   a retaining clip having retention barbs;
   a gasket configured to be compressed to provide a liquid-tight seal around an outer diameter of the needle assembly and the distal end of the syringe body;

a needle latch assembly, comprising:
  first and second latching tabs configured to retain the needle assembly in a close state and to be plastically deformed to an open state to release the needle assembly; and
  a gasket backstop configured to provide a flat surface for compression of the gasket, wherein the first and second latching tabs are spaced apart from the gasket such that neither of the first and second latching tabs contact the gasket during compression of the gasket; and
a needle hub having a plurality of interior surfaces configured to retain the needle latch assembly, the gasket, the retaining clip, and the distal end of the syringe body in a sealed configuration to prevent liquid from leaking to an exterior of the needle hub during injection using the syringe assembly,
wherein the needle assembly is configured to be retracted into the syringe body after injection using the syringe assembly.

2. The assembly of claim 1, the needle latch assembly further comprising:
a cage including:
  a flat body having a first opening defined therein, and first and second arms extending orthogonally from the flat body; and
  wherein the first and second latching tabs extend orthogonally from the first and second arms respectively and define a second opening,
  wherein the first opening is larger than the second opening,
  wherein the larger opening is sized and shaped to allow passage of the needle assembly therethrough, and
  wherein the second opening is sized and shaped to prevent passage of the needle assembly therethrough until the first and second latching tabs are deformed.

3. The assembly of claim 2, wherein the first and second latching tabs are plastically deformable.

4. The assembly of claim 3, wherein the first and second latching tabs are configured to plastically deform when 2 lbs. to 3 lbs. of proximally directed force is applied thereto.

5. The assembly of claim 2, wherein the first and second latching tabs are symmetrical.

6. The assembly of claim 2, wherein the first and second latching tabs are configured to engage with and disengage from a needle while remaining inside of the cage.

7. The assembly of claim 2, wherein the first opening is disposed at a center of the flat body.

8. The assembly of claim 2, wherein the second opening is disposed coaxially with the first opening.

9. The assembly of claim 2, wherein the first and second arms are elastically deformable.

10. The assembly of claim 2, wherein the first and second arms respectively include first and second pairs of standoffs at an opposite end of the cage from the flat body.

11. The assembly of claim 10, wherein the first and second pairs of standoffs are bent toward each other.

12. The assembly of claim 2, wherein the first and second arms are each arcuate when viewed axially.

13. The assembly of claim 2, wherein the flat body, the first and second arms, and the first and second latching tabs are stamped or cut as one piece from a sheet of metal.

14. The assembly of claim 1, the needle latch assembly further comprising:
  a top flat disc-shaped body having
    the first and second latching tabs defining a first opening, and
    a second opening, wherein the second opening is larger than the first opening defined therein;
  a bottom flat disc-shaped body having an ovoid opening defined therein; and
  a plurality of joining members coupled to the top and bottom flat disc-shaped bodies such that the ovoid opening defined in the bottom flat disc-shaped body is aligned with the first and second openings defined in the top flat disc-shaped body,
  wherein the second opening is sized and shaped to allow passage of the needle assembly therethrough, and
  wherein the first opening is sized and shaped to prevent passage of the needle assembly therethrough until the first and second latching tabs are deformed.

15. The assembly of claim 14, wherein the top and bottom flat disc-shaped bodies and the plurality of joining members are stamped or cut as one piece from a sheet of metal.

* * * * *